US008888697B2

(12) United States Patent
Bowman et al.

(10) Patent No.: US 8,888,697 B2
(45) Date of Patent: Nov. 18, 2014

(54) METHOD AND SYSTEM FOR ENABLING LAY USERS TO OBTAIN RELEVANT, PERSONALIZED HEALTH RELATED INFORMATION

(75) Inventors: Brad Bowman, Mableton, GA (US); Tushar Tanna, New York, NY (US); David Link, New York, NY (US); David Gang, Oakton, VA (US)

(73) Assignee: WebMD, LLC, New York, NY (US)

( * ) Notice: Subject to any disclaimer, the term of this patent is extended or adjusted under 35 U.S.C. 154(b) by 1350 days.

(21) Appl. No.: 11/491,861

(22) Filed: Jul. 24, 2006

(65) Prior Publication Data

US 2008/0021288 A1    Jan. 24, 2008

(51) Int. Cl.
| | |
|---|---|
| *A61B 5/00* | (2006.01) |
| *G06Q 10/00* | (2012.01) |
| *G06Q 50/00* | (2012.01) |
| *G06F 19/00* | (2011.01) |

(52) U.S. Cl.
CPC ............ *G06F 19/322* (2013.01); *G06F 19/345* (2013.01)
USPC .............................................. 600/300; 705/2

(58) Field of Classification Search
USPC ........... 600/300–301; 705/2–3; 709/203, 209, 709/227
See application file for complete search history.

(56) References Cited

U.S. PATENT DOCUMENTS

| | | | |
|---|---|---|---|
| 6,132,218 A | 10/2000 | Benja-Athon | |
| 6,270,456 B1 * | 8/2001 | Iliff | 600/300 |
| 6,767,325 B2 * | 7/2004 | Iliff | 600/300 |
| 7,149,756 B1 * | 12/2006 | Schmitt et al. | 1/1 |
| 7,464,021 B1 * | 12/2008 | Myers et al. | 704/7 |
| 7,512,575 B2 * | 3/2009 | Mahesh | 706/45 |
| 2001/0053875 A1 * | 12/2001 | Iliff | 600/300 |
| 2003/0212579 A1 * | 11/2003 | Brown et al. | 705/2 |
| 2004/0122790 A1 * | 6/2004 | Walker et al. | 707/1 |
| 2006/0004607 A1 | 1/2006 | Marshall et al. | |
| 2006/0167992 A1 * | 7/2006 | Cheung et al. | 709/204 |

FOREIGN PATENT DOCUMENTS

WO    WO 0185021 A1 * 11/2001

OTHER PUBLICATIONS

WO 01/85021 A1, Schmitt et al. "System and method for determining the probable existence of disease".*

* cited by examiner

*Primary Examiner* — William Thomson
*Assistant Examiner* — Shirley Jian
(74) *Attorney, Agent, or Firm* — Wilmer Cutler Pickering Hale and Dorr LLP

(57) ABSTRACT

The invention features methods, systems, and computer programs for generating a customized set of possible medical conditions, thereby providing access to medical information relevant to the user's state of health. The methods and systems involve at least some of the following steps: receiving a list of symptoms specified in terms selected from a first language set; translating the list of symptoms into a translated list of symptoms specified in terms selected from a second language set; using the translated list of symptoms to generate possible medical conditions, the possible medical conditions described in terms of the second language set; and translating the possible medical conditions into descriptions that are specified in terms selected from the first language set.

29 Claims, 22 Drawing Sheets

| Geographic location information | Number of users concurrently reporting 4 or more of the following typical influenza symptoms: fever, sore throat, muscle aches, headache or fatigue |
|---|---|
| NYC | 100 |
| DC | 85 |
| ATL | 35 |
| SEA | 40 |
| KC | 50 |

FIG. 12A

| Geographic location information | Number of users concurrently reporting 4 or more typical influenza symptoms AND 1 or more of the following atypical symptoms: conjunctivitis (eye infection), breathing problems (pneumonia, acute respiratory distress, viral pneumonia, chest pain or diarrhea and confusion (without breathing problems) |
|---|---|
| NYC | 5 |
| DC | 1 |
| ATL | 2 |
| SEA | 3 |
| KC | 0 |

FIG. 12B

How would you describe your chest pain?
    [ ] sharp
    [ ] dull
    [ ] hot or burning
    [ ] squeezing, heaviness or pressure
    [ ] tearing
    [ ] other

How did your chest pain begin?
    ( ) instantly
    ( ) rapidly
    ( ) gradually

FIG. 14

| CLINICAL MEDICAL TERM OR TERMS | LAY MEDICAL TERM | Concept-Specific Identifier |
|---|---|---|
| GUARDING OF THE ABDOMEN-INVOLUNTARY | ABDOMEN SENSITIVE TO TOUCH | C0238547 |
| NIPPLE DISCHARGE, ABNORMAL | ABNORMAL NIPPLE DISCHARGE | 00149741 |
| ADRENALIN-TEST | ADRENALIN LEVEL | C0201998 |
| AMINOPHYLLINE, SERUM | AMINOPHYLLINE LEVEL | C0002575 |
| AMITRIPTYLINE, SERUM | AMITRIPTYLINE LEVEL | C0202316 |
| AMMONIA - TEST | AMMONIA LEVEL | 00201879 |
| SALICYLATE, SERUM | ASPIRIN LEVEL | 00202463 |
| CONGENITAL BAND SYNDROME | BABY BANDS | C0270724 |
| URINATION, BED WETTING | BED WETTING | 00014394 |
| OROPHARYNX LESION BIOPSY | BIOPSY OF THROAT | 00192211 |
| PERIODS, MENSTRUAL - BLEEDING BETWEEN | BLEEDING BETWEEN MENSTRUAL PERIODS | 00302811 |
| EAR DISCHARGES/BLEEDING | BLEEDING FROM EAR | 00271412 |
| HCG (QUALITATIVE - SERUM) | BLOOD HCG LEVEL | 00430064 |
| HEMOGLOBIN, SERUM | BLOOD HEMOGLOBIN LEVEL | 00523685 |
| LEAD - SERUM | BLOOD LEAD LEVEL | 00524167 |
| LITHIUM, SERUM | BLOOD LITHIUM LEVEL | 00337452 |
| BORN WITH AN OPTIC DISC ABNORMALITY | BORN WITH AN ABNORMAL OPTIC NERVE | 00521571 |
| TACHYPNEA | BREATHING FAST | C0231835 |
| BACKBONE FRACTURE | BROKEN BACK | 00080179 |
| METACARPAL FRACTURE | BROKEN METACARPAL | 00272677 |
| SACRUM/COCCYX FRACTURE | BROKEN TAILBONE | 00149860 |
| MONOPLEGIA OF LOWER EXTREMITY | CAN'T MOVE LEG | 00154702 |
| DYSURIA | PAIN WITH URINATION | 00028961 |
| VISION, NIGHT BLINDNESS | CAN'T SEE AT NIGHT | 00028077 |
| INABILITY TO SLEEP | CAN'T SLEEP | 00021603 |
| SMELL, IMPAIRED | CAN'T SMELL | 00481703 |
| MEDIAN NERVE RELEASE | CARPAL TUNNEL SURGERY | C0196576 |
| HOARSENESS OR CHANGING VOICE | CHANGING VOICE | 00518179 |
| CHEST LACERATION | CHEST CUT | C0432951 |
| HICCUPS, CHRONIC | CHRONIC HICCUPS | 00019521 |
| CHRONIC PAIN AND FATIGUE CONDITION | CHRONIC PAIN | 00150055 |
| DIURETIC | WATER PILL | C0033231 |
| HYDROXYZINE INJECTION | CORTISONE SHOT | C0010137 |
| COMPUTERIZED TOMOGRAPHY OF ORBIT | CT OF EYE SOCKET | 00202754 |
| CXR | CHEST XRAY | 00202783 |
| FRACTURE | BROKEN | 00016658 |
| DIABETES MELLITUS | SUGAR DISEASE | 00011849 |

FIG. 15

| Condition | Severity | Age | Symptom | Symptom Body Part | Clarification | Clinical Alert |
|---|---|---|---|---|---|---|
| Strep Throat | Medium | All | Fever | All | None | See doctor 1-2 days |
| Strep Throat | Medium | All | Swollen Glands | Throat | 1.) Both sides or just one? | See doctor 1-2 days |
| Strep Throat | Medium | All | Cough | Throat | 1.) Constant or intermittent cough? | See doctor 1-2 days |
| Strep Throat | Medium | All | Excessive Sweating | All | None | See doctor 1-2 days |
| Strep Throat | Medium | All | Headache | Head | 1.) Sudden onset? 2.) Recent head injury? | See doctor 1-2 days |

FIG. 16

METHOD AND SYSTEM FOR ENABLING LAY USERS TO OBTAIN RELEVANT, PERSONALIZED HEALTH RELATED INFORMATION

BACKGROUND OF THE INVENTION

Consumer health information is growing in importance and popularity, with computer networks such as the Internet providing a growing share of the information. It is estimated that health issues are addressed at tens of thousands of online sites with potentially millions of pages of health or benefit-related works. Even more health related information exists on networks available to medical professionals. Given the volume and complexity of the available medical information, lay consumers without specific medical training are at a disadvantage and can have relatively little success in finding desired or relevant information among such vast resources.

Moreover, given the extremely personal nature of health, most individuals have minimal interest in browsing materials that have no relevance to their health or the health of their families. Yet most of the health information accessible to the lay public exists on conventional network (e.g., Internet) sites or portals and addresses only general topics. Such information seldom has any particular relevance to individual users. Accordingly, there is a need for improved systems for obtaining relevant, personalized health related information from computer networks such as the Internet.

SUMMARY OF THE INVENTION

In one aspect, the invention features methods, systems and computer programs for generating a customized set of possible medical conditions. The methods and systems involve the steps of: receiving a list of symptoms specified in terms selected from a first language set; translating the list of symptoms into a translated list of symptoms specified in terms selected from a second language set; using the translated list of symptoms to generate possible medical conditions, the possible medical conditions described in terms of the second language set; and translating the possible medical conditions into descriptions that are specified in terms selected from the first language set. The generated possible medical conditions correspond to the translated list of symptoms.

In another aspect, the invention features methods, systems and computer programs for generating input for a health condition query system. The methods and systems involve the steps of: presenting a representation of a human body to a user through a visual display; defining a plurality of regions within the representation of the human body; receiving input from the user selecting a particular one of the plurality of regions; in response to the received input, displaying to the user a list of health symptoms associated with the selected region; enabling the user to select multiple symptoms from the displayed list of symptoms; and presenting a list of possible medical conditions derived from the plurality of medical symptoms. In some implementations, the methods, systems and computer programs include enabling the user to select the orientation of the representation of the human body.

In another aspect, the invention features methods, systems and computer programs for tracking possible medical conditions. This aspect involves the steps of: providing an interface to a query engine, which in response to receiving symptom information from a plurality of users provides a personalized list of possible diagnostic information to each of the plurality of users; receiving input through the interface to the query engine from each of the plurality of users, the input from each user comprising health symptom information and geographic location information; and analyzing the symptom information and the geographic location information for the plurality of users to determine medical conditions as a function of geographic area.

In some implementations, the second language set is professional medical language comprising professional medical terms that describe symptoms and conditions. Likewise, in some embodiments of the above aspects, the first language set is non-professional medical language, comprising medical terms used by laypeople to describe medical symptoms or conditions. In some implementations, the methods and systems also involve the steps of querying for additional symptom information based on one or more of the following: one or more symptoms, one or more possible medical conditions, or one or more symptoms and one or more possible medical conditions; and adding the additional symptom information to the list of symptoms.

The methods, systems, and computer programs described herein are not medical diagnostic systems and are not intended to take the place of evaluation by a trained medical professional. Rather, these systems and methods provide users access to medical information and help direct users to medical information that may be relevant to the their state of health.

The methods, systems, and computer programs described herein provide the advantage of delivering relevant, customized health-related information to consumers. The methods, systems, and computer programs provide consumers access to expert, professional medical information systems which, due to vocabulary requirements, are not typically accessible to laypeople without medical training. The methods, systems, and computer programs also provide consumers an improved ability to identify detailed medical information on a particular topic that is relevant to their state of health. Because identifying relevant medical information requires understanding the relationships between symptoms and conditions, this information is typically difficult for consumers who do not have medical training. The methods and systems also provide the ability to analyze medical information taken directly from a large population of users, thereby improving the immediacy and quality of the information.

The details of one or more embodiments described herein are set forth in the accompanying drawings and the description below. Other features, objects, and advantages of the invention will be apparent from the description and drawings, as well as from the claims.

BRIEF DESCRIPTION OF THE DRAWINGS

FIGS. 12A and 12B are exemplary output for a medical information tracking system in tabular format.

FIG. 14 is an exemplary clarification question interface.

FIG. 15 is a table with medical terms in professional and non-professional language and associated concept-specific identifiers.

FIG. 16 is a table representing a data structure of relationships between conditions, symptoms, clarification questions, and other medical information.

DETAILED DESCRIPTION

Figure 1:
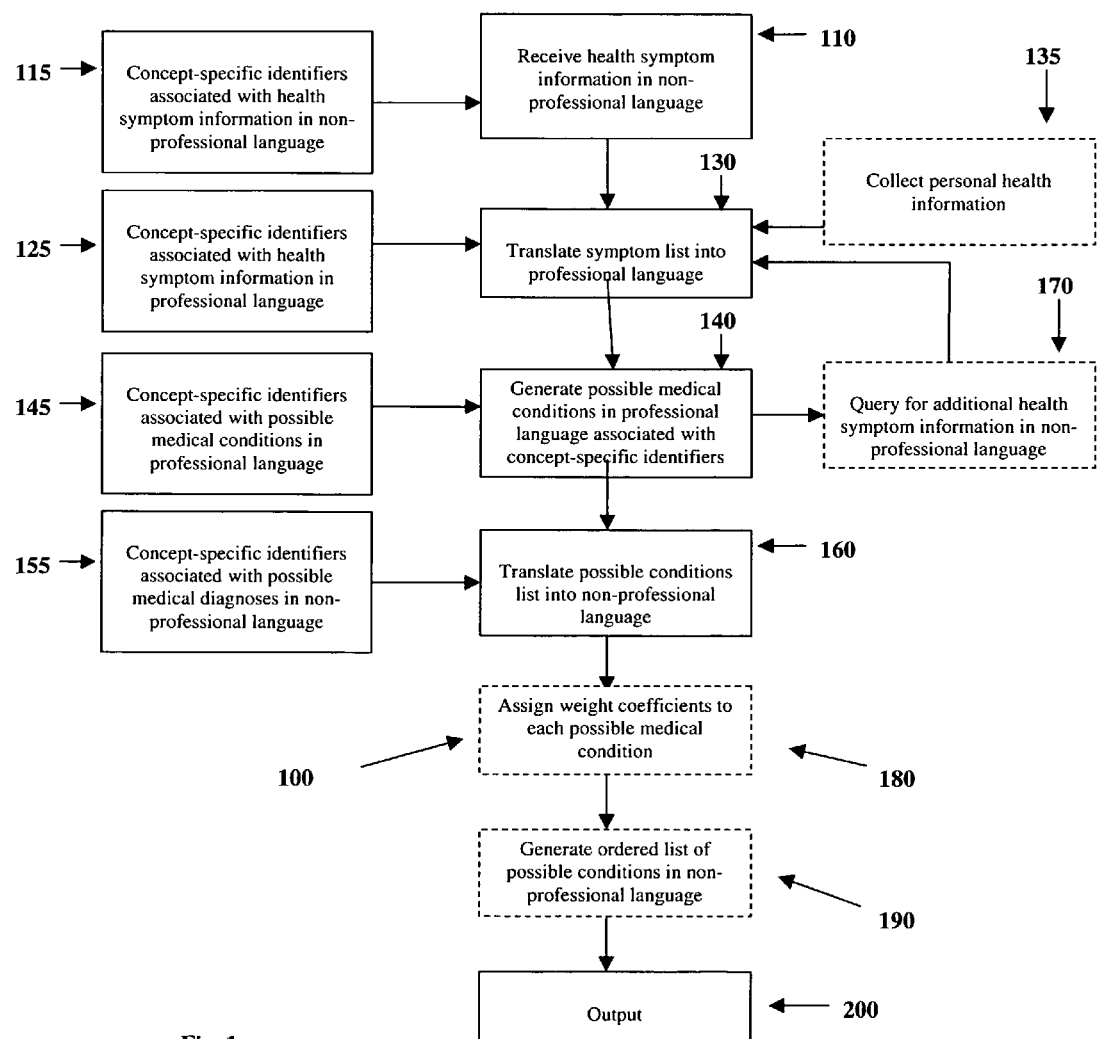
FIG. 1 is a flow diagram of one implementation of a health condition query system.
Figure 18:
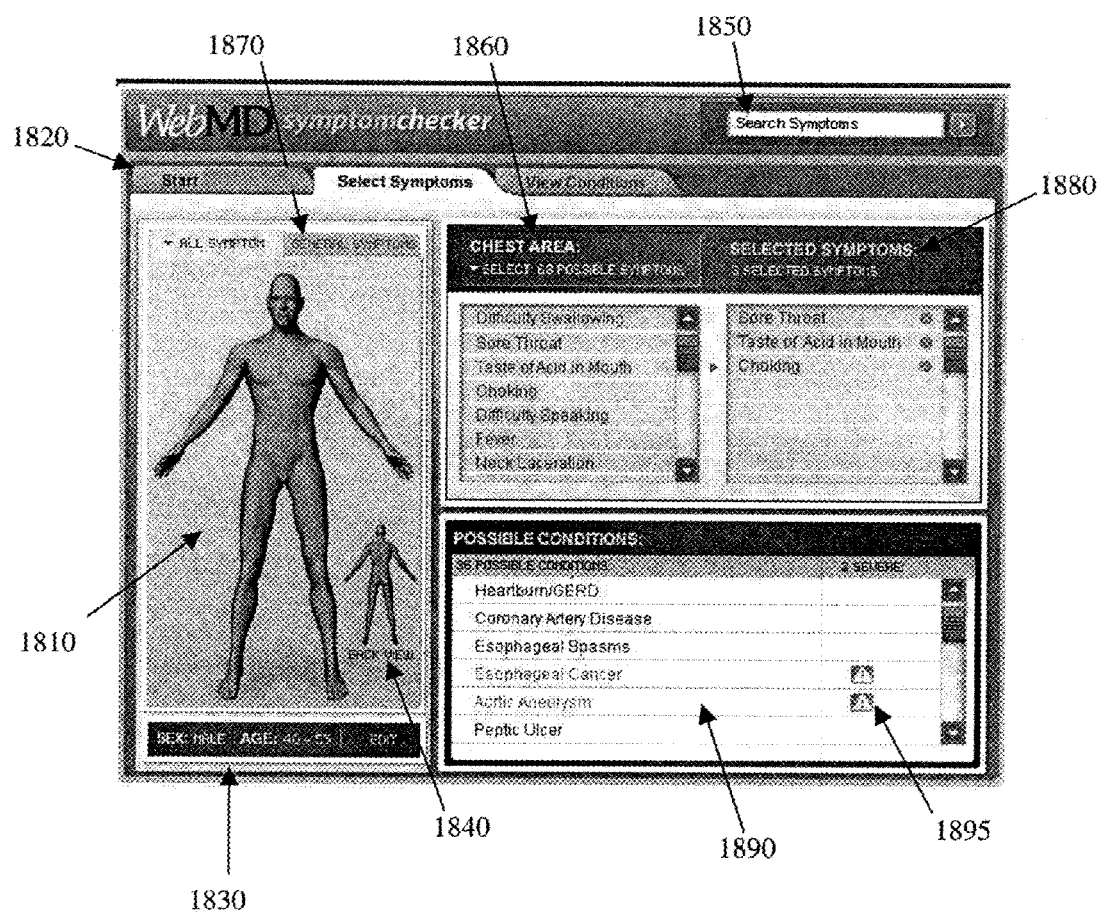
FIG. 18 is an exemplary health condition query system interface.

FIG. 1 is a flow diagram of a health condition query system 100 that generates a list of possible medical conditions according to one embodiment of the invention. The system collects health symptom information from the user. It does this by presenting a graphical user interface that solicits the relevant input. FIG. 18 is an example of a user interface for such a health condition query system. The user then inputs the information into the system (step 110). Referring to FIG. 18, in one implementation, the user inputs health symptom information by selecting from a list of possible symptoms for a given area of the body (1860). The system generates a list of selected symptoms (1880) based on the user's input.

Health symptom information includes information about the user's state of health, such as indications or manifestations of a physical condition or disease. Nonlimiting examples of health symptom information include headache, sore throat, congestion, fever, cough, earache, nausea and muscle cramp. The user expresses the health symptom information in terms selected from a first language set. One exemplary language set is non-professional medical language. Non-professional medical language includes terms used by laypeople (i.e., people who do not have a medical education) to describe a medical symptom or complaint. For example, a layperson may describe a symptom as headache, while the medical professional term for that symptom is cephalgia. Accordingly, "headache" is considered a term selected from a non-professional language.

A translation engine translates the symptom list from the first language set to a second language set (step 130). One exemplary language set is professional medical language, which includes terms used by medical professionals (i.e., people with a medical education, such as physicians, nurses, and mental health professionals). Professional language includes terminology a medical professional would use to describe medical symptoms or conditions. Such terms include those found in medical dictionaries, thesauri, and encyclopedias. For example, "cephalgia" is a term selected from medical professional language for the symptom "headache." Translation proceeds through correlation of concept-specific identifiers that are associated with the health symptom information in terms selected from both language sets. In the example above, the concept-specific identifiers are associated with terms selected from non-professional language (step 115) and professional language (step 125).

The association of concept-specific identifiers with health symptom information is shown in steps 115 and 125. A symptom thesaurus algorithm associates concept-specific identifiers with symptoms, such that each symptom expressed in non-professional language is uniquely associated with an identifier (step 115). Similarly, concept-specific identifiers are associated with health symptom information expressed in professional language (step 125).

The thesaurus is stored on a computer-readable medium and provides the concept-specific identifiers based upon the symptom or condition terms. The thesaurus incorporates terminology from many health-related vocabularies, including the Systematized Nomenclature of Medicine (SNOMED) promulgated by the College of American Pathologists; the International Classification of Diseases: 9th revision, Clinical Modification (ICD9), promulgated by the Health Care Financing Administration, as well as the Consumer Health Terminology® created by WellMed, Inc (now WebMD, Inc.); and the Unified Medical Language System (UMLS®), promulgated by the U.S. National Library of Medicine, which also provides concept-specific identifiers.

The concept-specific identifiers are based on core medical concepts, enabling the thesaurus algorithm to map or associate multiple synonyms and related terms to the same concept-specific identifier or code. For example, "erythemia", "hyperemic", "injected", "rugor", and "erythematous" are all used in professional circles to describe the same thing: redness or red-color. Similarly, "odynophagia" and "dysphagia" are used both used to describe difficulty in swallowing. With respect to conditions, "hyperpiesis," "elevated systolic pressure," "high blood pressure", "hypertensive vascular disease" and "high blood" are all used in consumer and professional circles to describe the same thing: high blood pressure. Accordingly, the thesaurus algorithm maps all these terms with a single concept-specific identifier.

The concept-specific identifiers provide standardized identification of the health symptom information independent of traditional variations between lay medical and clinical medical terminology for heath conditions. For example, the thesaurus algorithm associates the symptom chest pain with the concept-specific identifier: C0008031. It further correlates the symptom with ICD9 code 786.50. Similarly, the thesaurus algorithm associates abdominal pain with the concept specific identifier C0000737 and ICD9 code 789.00. As shown above, in one implementation, the concept-specific identifiers are in the form of alpha-numeric segments (e.g., 8 characters each). Alternatively, numeric or alphabetic segments are used.

As part of generating a translated symptom list, the health condition query system also optionally collects additional personal health information from the user (step 135). In some implementations, the system imports the personal health information from another resource, such as the user's stored profile or health record information that is stored in a computer-accessible manner (e.g., electronic health records stored at a physician site, electronic health records stored at an insurance site, and hospital admission records). Alternatively, the system presents input screens that solicit the desired information from the user. The personal health information includes further information about the user's state of health. The personal health information includes information that affects or has affected the health of the user or that is part of the user's health history. Exemplary personal health information includes, without limitation, allergies, medical test information (e.g., blood tests, genetic tests and radiology consult reports), medications, health risks, vaccinations, surgeries or procedures, known medical diagnoses, family history, past symptom information, and past medical condition information generated from a health condition query system. The personal health information may also include demographic information about the user that is useful for determining possible medical conditions. Such information includes, without limitation, gender, age, and geographic location. The personal health information may also be correlated with concept-specific identifiers. Referring to FIG. 18, the information includes the sex and age of the user (1830), which the user provides through an input interface (e.g., the "Start" tab (1820)).

In addition to additional personal health information, in some implementations, the system collects health-related information from external sources, such as information from public health organizations, such as the Centers for Disease Control (CDC). One nonlimiting example of such information includes CDC reports providing information about health conditions occurring in particular areas. If this information correlates with the geographic information provided by the user, it is included in the information used to generate the list of possible medical conditions. For example, if the CDC (or other public health organization), reports an increase in influenza in a particular area, the health condition query system will use that information when constructing the list of possible diagnoses for the user, if the user is also located in the affected area. Similarly, other external health information received by the health condition query system includes weather information that may affect medical conditions (e.g., downloaded from the National Weather Service or commercial services such as Weather.com) or information from a health condition tracking system such as the tracking system described herein (e.g. FIGS. 7 and 8). In some implementations, the health condition query system also translates the information from external sources (i.e., not generated from the user's input) from a first language to a second language as described above.

Once the health condition query system generates a translated symptom list (step 130), the system generates possible medical conditions based on those symptoms (step 140). Symptoms and possible conditions are mapped to one another in a database in a many to many relationship. The system identifies possible conditions by correlation to one or more symptoms. In some implementations, the data is stored in the database as shown in FIG. 16. The possible medical conditions are generated in professional language and are also associated with concept-specific identifiers (step 145). For example, appendicitis is associated with concept-specific identifier C0003615 and ICD9 code 541, while cholecystitis is appendicitis is associated with concept-specific identifier C0008325 and ICD9 code 575.10.

In some implementations, once the system generates an initial list of possible medical conditions, a clarification engine queries the user for additional symptom information (step 170). The system presents the queries to the user through a graphical user interface. In this process, the clarification engine includes a library of clarification questions that are mapped to particular conditions. When the health condition query system adds a possible condition to the list of possible medical conditions, the clarification engine prompts the user for additional information related to that condition. The system adds the additional health symptom information to the symptom list, which is then used to refine the generated list of possible conditions. The library maps one or more clarification questions to a particular condition or combination of conditions. Generally, there is no restriction on the number of clarification questions. In some specific implementations, one to five clarification questions are mapped to a condition. For example, the clarification engine links the condition "appendicitis" to one or more clarification questions such as "Do you have a fever?" or "Do you have nausea?" or "Do you have vomiting?" The engine may also query the user for additional information based on a combination of conditions and symptoms. For example, if the health condition query system generates cholecystitis (inflammation of the gall bladder) as a possible condition and the user has also included abdominal pain as a symptom, the clarification engine will ask the user: "Is your abdominal pain better or worse after meals?" If the answer is "worse", the system either adds gallstones to the list of possible conditions or increases the likelihood of that condition (e.g., increases its weight coefficient as described below), as these are highly correlative. However, an answer of "better" or "no change" is neutral. In this case, the system may leave gallstones from the list of possible conditions, but not change the likelihood of the condition. Alternatively, the system may remove gallstones from the list of possible conditions or decrease the likelihood of that condition (e.g., decreases its weight coefficient).

The clarification engine generates queries either at the time the condition is identified as a possible condition or after the possible conditions list is complete. While clarification questions are generally optional and the user may choose not to answer, in some implementations, the system does not add the possible condition to the conditions list until the user answers the clarification questions. Clarification questions are generally limited to general signs and symptoms that the user can recognize without the need for a physician office visit. Clarification questions thus provide additional information upon which system generates possible medical conditions. As more symptom information is added and refined, the list of possible conditions is more specific for the user's state of health.

The translation engine translates the possible medical conditions from the second language set to the first language set (e.g., from professional language to non-professional language) (step 160) in a process similar to the process described above for the health symptom information. Specifically, it associates concept specific identifiers with possible medical conditions in non-professional language. It then correlates concept-specific identifiers for each language to produce a translated list of possible medical conditions in non-professional language.

In some implementations, after translating the list of possible conditions, the health condition query system assigns a weight coefficient to each possible state of health (step 180). Weight coefficients relate to the probability of one possible condition versus another being applicable to the user's medical state (i.e., the likelihood of that condition). The system derives weight coefficients empirically, using information collected during the generation of the symptom list and employing sets of rules stored in a database associated with the health condition query system. The rules take into account one or more criteria for assigning weight coefficients. One criterion is clustering or pattern recognition of symptoms to possible conditions. For example, if a possible condition is associated with five symptoms, the system assigns a higher weight coefficient when the symptom list includes four of the symptoms, compared to when it has just one of the symptoms.

A second criterion for assigning weight coefficients is the specificity of a symptom or group of symptoms for a condition. Specificity is based on population statistics of conditions and correlates with the frequency of people having a particular symptom. For example, for a particular condition, if a high percentage of people who are ultimately diagnosed with the condition typically present with a specific symptom, the symptom is considered highly specific for the condition. Accordingly, where these symptoms are present, the system assigns a higher weight coefficient to these conditions. Alternatively, if only a few people diagnosed with the condition typically present with a particular symptom, it is considered relatively non-specific and the system assigns a lower weight coefficient to the associated condition. In some implementations, the system categorizes specificity levels for symptoms. For example, some symptoms are always correlated with a condition and are therefore highly specific. If a user presents with these symptoms, the system assigns the correlating condition a relatively high weight coefficient. Other symptoms usually or typically occur with a particular condition. Because these symptoms are less specific for the condition, the system assigns the condition a lower weight coefficient when this class of symptoms are the only symptoms present on the symptom list. Finally, some symptoms are only sometimes or infrequently correlated with a condition. When these are the only symptoms present for the condition, the system assigns this condition the lowest weight coefficient. Both specificity and clustering can also take into account other medical information, such as age, gender, race, ethnic group and weight.

Another weighting criterion is based on exclusion symptoms. Exclusion symptoms are symptoms that exclude a possible condition. For example, if a user inputs "sore throat" and "cough", one possible condition is strep throat. If, however, through clarification questions, the user indicates that the cough is a productive cough, the weight coefficient for strep throat is lowered (or the condition is even eliminated from the list), because productive coughing is not a symptom of strep throat; only non-productive coughs are a strep throat symptom.

In situations where a symptom is pathoneumonic for a possible condition (i.e., the symptom is 100% correlated with the condition), it may be categorized as a key or critical symptom. For example, a Fifth's disease rash (a red rash on the cheek) is pathoneumonic, as is a Lyme's disease rash (a bull's eye-shaped rash). Similarly, if a user indicates that his leg is shortened and also rotates, these symptoms are pathoneumonic for fracture. When such symptoms are present, the system maximizes the weight coefficient maximized and, may, in some implementations, eliminate other, less specific, possible conditions from the list.

Other criteria for assigning weight coefficients include geographical location information (where conditions associated with a particular geographical location are assigned a higher weight coefficient if the user is also associated with that location), current medications (imported and self-reported), and information from external sources. External sources include reports from public health organizations, (e.g., CDC), weather related information, or information from a health tracking system such as the condition tracking system described herein. The health condition query system assigns weight coefficients based on one or more of these criteria. For example, in one implementation, the system looks for clusters of symptoms, giving conditions that have more symptoms present a higher coefficient. Next, the system examines the symptom list for exclusion symptoms, to determine if any conditions can be removed from the possible condition list (or its weight coefficient reduced) due to the presence of an exclusion symptom. Lastly, the system evaluates the symptom list for specificity, increasing the weight coefficient for conditions having multiple key symptoms and decreasing the weight coefficient for conditions only presenting symptoms that are less specific (i.e., those that only sometimes correlate with the condition). With regard to information collected from external sources, the system may increase a weight coefficient for the "influenza" if CDC reports indicate a rise in the incidence of influenza in the California and the user has indicated that she is experiencing coughing and is also located in California. Similarly, if a user indicates she is experiencing red eyes and sneezing and is located in Virginia, the health condition query system may download information from a health tracking system (such as the condition tracking system described herein) that indicates an increase in the incidence of seasonal allergies in the southeast United States. In this situation, the health condition query system increases the weight coefficient for seasonal allergies.

In addition to weight coefficients for the likelihood of conditions, in some implementations, the system also assigns weight coefficients for the acuity or urgency of the condition. Acuity or urgency is an estimate of how quickly a condition may manifest based on the information in the symptom list. The urgency weight coefficient is separate from the weight coefficient for the likelihood of the condition and, in some implementations, the system may not alter the ordered list of possible conditions based on the urgency weight coefficient. Instead, in some implementations, the system alters the output of the list of possible conditions to alert the user that a highly urgent or acute condition is present. For example, the system adds a marker or icon to conditions associated with highly urgent or acute conditions, based on the urgency weight coefficient (e.g., the caution icon (1895) in FIG. 18).

In some implementations, the system also assigns weight coefficients for the severity of the condition. Severity is an estimate of the seriousness of the condition, or the extent of possible harm that may result from the condition. The severity weight coefficient is also separate from the weight coefficient for the likelihood of the condition. In some implementations, severity weight coefficient is also separate from the urgency weight coefficient, while in some implementations the system combines the severity and urgency weight coefficients. As with the urgency coefficient, in some implementations, the system may not alter the ordered list of possible conditions based on the severity weight coefficient. Instead, in some implementations, the system alters the output of the list of possible conditions to alert the user that a severe condition is present. For example, the system adds a marker or icon to conditions associated with severe conditions, based on the severity weight coefficient (e.g., the caution icon (1895) in FIG. 18). Similarly, when the system combines the urgency and severity coefficients, it may use a single marker or icon to alert the user that a severe and/or urgent condition is present. External information downloaded or otherwise received by the health condition query system may also be used to assign urgency and/or severity coefficients.

Once the system assigns weight coefficients to the possible medical conditions, it generates an ordered list of the possible conditions and outputs the results (steps 190 and 200). An example of a list of possible conditions generated based on a user's selected symptom information is shown in FIG. 18 (1890).

Figure 2:
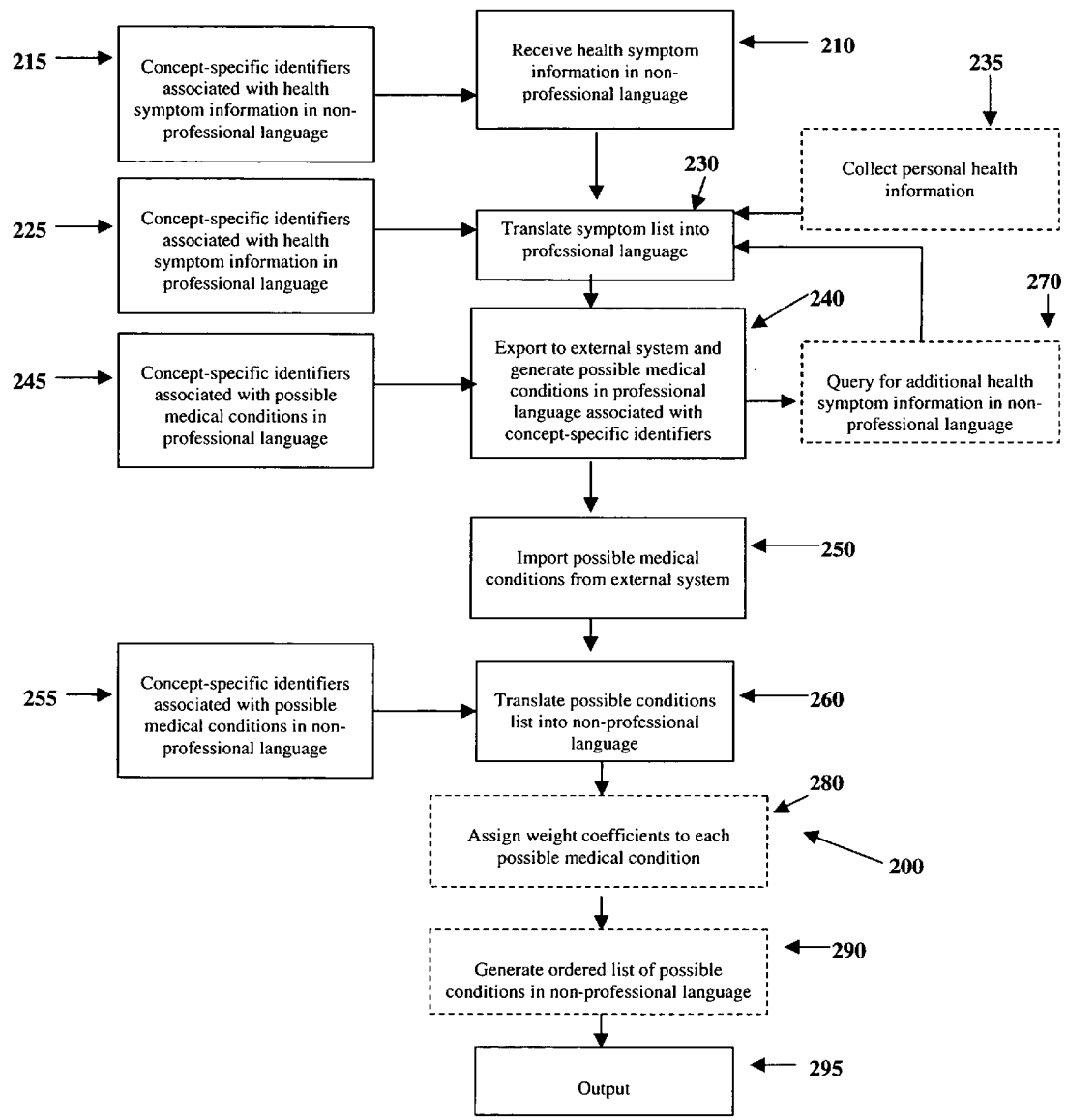
FIG. 2 is a flow diagram of one implementation of a health condition query system, in which information is exported to an external system.

FIG. 2 is a flow diagram of a health condition query system 200 similar to system 100 in FIG. 1, in which an external system is used to generate the list of possible conditions. System 200 begins as described above for process 100 (FIG.

1). The system collects health symptom information and a translation engine translates the information from non-professional to professional language through correlation with concept-specific identifiers (steps 210, 215, 225, and 230). The system also optionally collects additional personal health information to add to the symptom list (step 235). Health condition query system 200 then exports the translated symptom list to an external system, which generates a list of possible medical conditions (step 240). In some implementations, the external system is a professional medical system designed to accept professional medical information. Exemplary professional systems include expert diagnostic systems, medical triage systems, predictive modeling systems, health risk assessment systems, drug interaction checker systems, benefit or plan comparison tools, health cost estimator tools, and health cost financial planning tools. As such, the external system generates the possible medical conditions in terms selected from professional language. The possible medical conditions are also associated with concept-specific identifiers. The external system then imports the possible medical conditions back to system 200 (step 250), which translates the conditions into non-professional language according to a process described above for system 100 (step 260). In some implementations, the system assigns a weight coefficient (step 280), and generates an ordered list of possible medical conditions (step 290). Lastly, the system outputs the generated possible medical diagnostic information (step 295). By translating health symptom information into professional language, system 200 provides lay people the advantage of accessing professional information and systems without requiring them to master the professional lexicon, which is often a prerequisite to using these systems.

Figure 3:
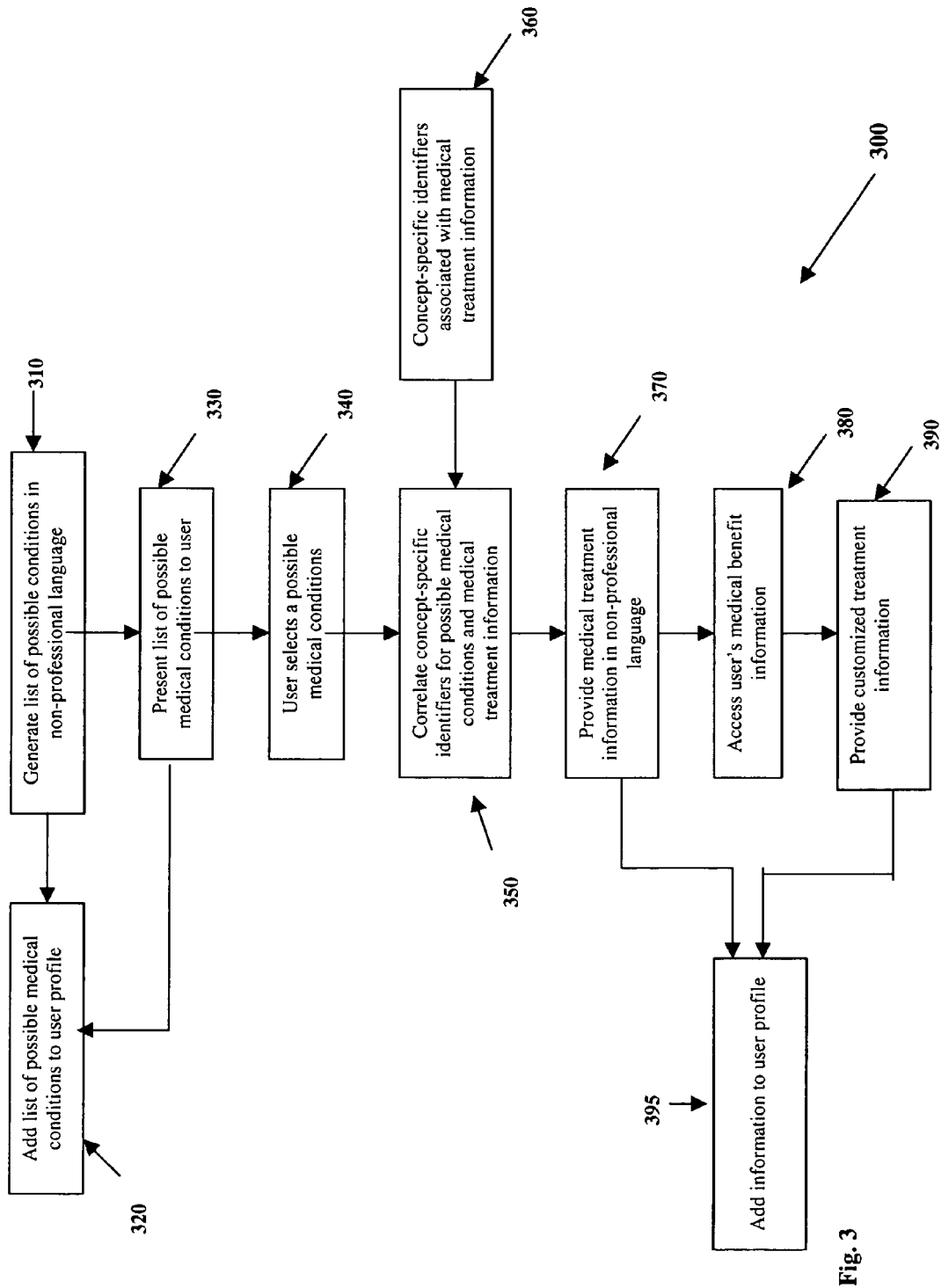
FIG. 3 is a flow diagram of an output algorithm for a health condition query system.

FIG. 3 is a flow diagram of an output generator (300) that augments health condition query systems 100 and 200 (FIGS. 1 and 2) by generating output for the systems. As described above, health condition query systems 100 and 200 generate a list of possible conditions in terms specified in non-professional language (steps 190 and 290 of FIGS. 1 and 2, respectively). The output generator begins with this information (step 310) and outputs the list of possible conditions in numerous ways. For example, in one implementation, a server creates and maintains one or more user profiles and the output system adds the list of possible medical conditions to the user profile (step 320). The user profile can be implemented as described in U.S. patent Publication No. 2006/0004607, which is incorporated by reference. The profile may contain information collected from the user, including symptoms, conditions, medications, test results, and demographic information. The user profile may also contain concept-specific identifiers associated with the information in the user profile. The profile may be periodically updated to reflect actions taken by the user, including creating new symptom and conditions lists.

Once saved, the generator optionally delivers medical text information to users on an automated basis, using the saved symptom list information. For example, the output generator matches attributes (e.g., health-related conditions) associated with the user with metadata (e.g., concept-specific identifiers) associated with medical text information loaded onto the server. As matches between the information in the user's profile and the metadata associated with the text information become available, the output generator automatically delivers the information to the user. A health condition query system can also access the information stored in the user profile to generate additional possible condition lists, for example by combining the stored information with new symptom information. For example, a user may create a symptom list that includes numbness and tingling of the extremities. If the user's stored profile information includes diabetes as a known medical diagnosis, is included in the algorithm and diabetic neuropathy will be added to the list of possible conditions presented to the user, even though the user did not input this information as a medical symptom himself. Thus, the health condition query system is able to provide users with output that is relevant to their medical history, which is useful where a user may not understand that current medical symptoms are relevant to a previous diagnosis.

Figure 9:
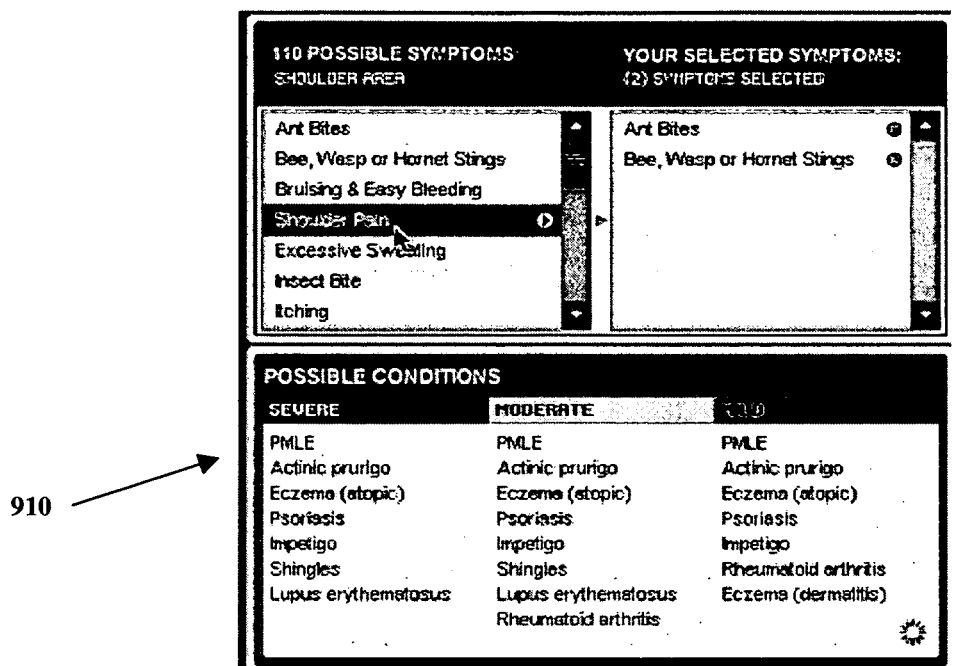
FIG. 9 is an exemplary translated symptom list and possible medical conditions list.

In another output option, output generator 300 presents a list of possible medical conditions directly to the user (step 330). FIG. 9 is an example of a possible condition list (910) presented through a graphical user interface. As shown in FIG. 9, in some implementations, the output system categorizes the list of possible conditions based on the severity of the conditions and presents the results in a tabular format. Similarly, FIG. 18 depicts a list of possible conditions (1890) correlating to the selected symptoms (1880) of sore throat, taste of acid in mouth, and choking.

Figure 11:
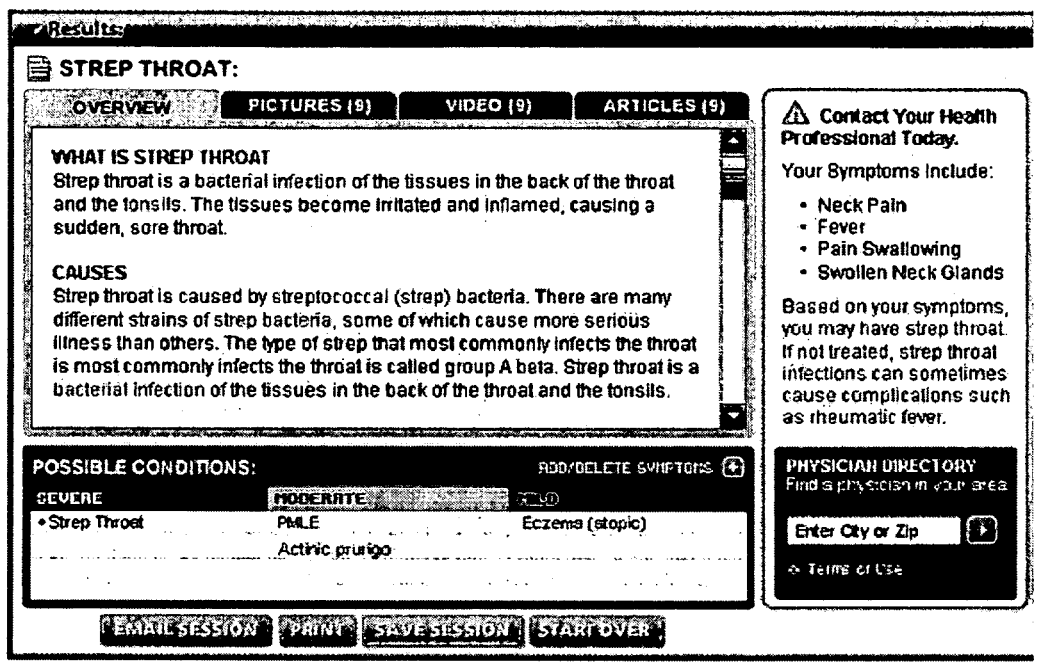
FIG. 11 is an exemplary output interface.
Figure 22:
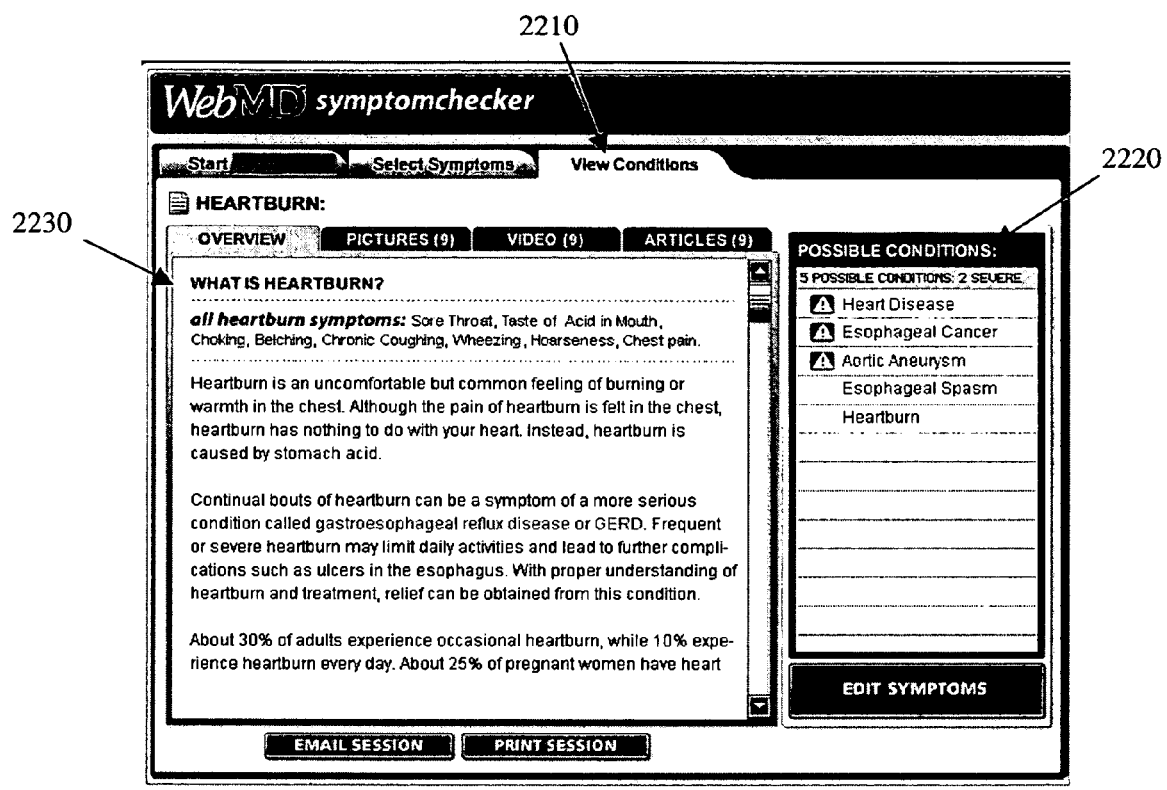
FIG. 22 is an example of output for a health condition query system.

After presenting the list of possible medical conditions to the user, the output generator then invites the user to select a particular medical condition that the user desires more information (step 340) through hyperlinks in a graphical user interface. Based on this selection, the generator provides medical treatment information in non-professional language to the user (step 370). Output generator 300 provides this information by correlating the concept-specific identifiers for the possible medical conditions with concept-specific identifiers that have been previously associated with medical treatment information (steps 350 and 360). The medical information includes without limitation a general overview of the medical condition, indication of symptoms, and treatment options. FIG. 11 is an example of output provided to the user for strep throat. FIG. 22 is an example of output provided to the user for heartburn. As shown in FIG. 22, upon selecting the "View Conditions" tab (2210), the user is presented with the list of possible symptoms correlating to his or her condition (2220). In the example of FIG. 22, when the user selects "heartburn", system provides various information about the health-related condition (2230). As shown in FIG. 22, the health-related information content includes, without limitation overview, pictures, video, and articles. Treatment options available as output with generator 300 include, without limitation, medications used to treat the condition, information about physicians who typically treat the condition, and cost estimates for one or more treatment plans (e.g., based on local and/or national averages). The output generator can further access the user's medical benefit information (step 380) to provide customized treatment information to the user (step 390). For example, the medical benefit information can include physician referral information. By accessing the user's medical benefit information, the generator determines the physician network to which the user belongs or to which the user has access through his or her health plan. The generator then correlates that information with the selected health-related condition, and provides a list of all doctors within the user's network who treat the selected health-related condition. Similarly, the output generator can access the user's insurance benefit information to provide a customized report of expected treatment costs (both out-of-pocket costs and total costs for both the patient and the insurer), contracted benefit information, and a listing of medications on the user's health plan formulary (including a comparison with all medications available for treatment) for the condition. As with the list of possible medical conditions, the personalized treatment information can also be saved to the user's profile (step 395).

Figure 5:
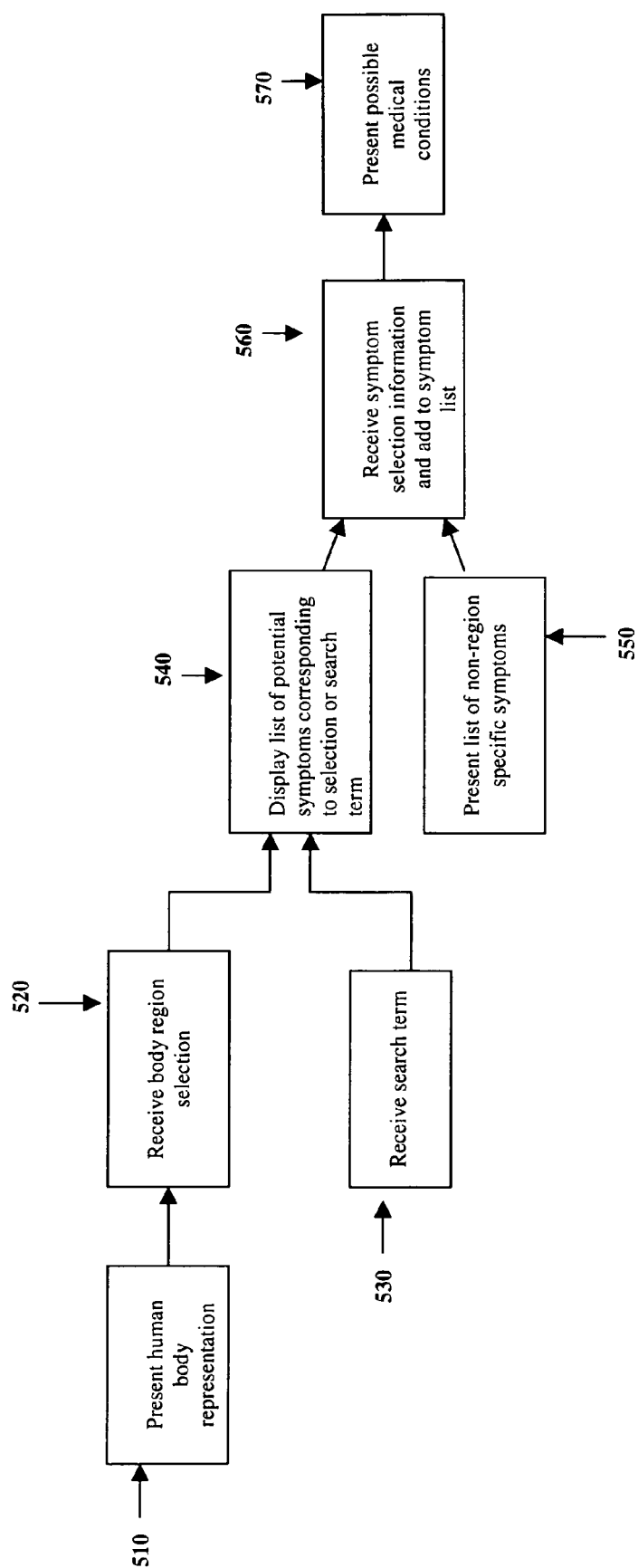
FIG. 5 is a flow diagram of a user interface algorithm according to one embodiment of the invention.

FIG. 5 is a flow diagram of the operation of an input generator for a health condition query system. Exemplary health condition query systems used with the process of FIG. 5 are the systems described above, as shown in FIGS. 2 and 3. The input generators provide three modes for generating input, as shown in steps 510, 530, and 550.

In step 510, a human body representation is presented to a user via a computer display. FIG. 18 is a representative interface for a health condition query system showing a human body representation according to step 510 (1810 of FIG. 18). In some implementations, the generator invites the user to select a specific human body representation (e.g., unisex, male or female). In the example of FIG. 18, a male representation has been selected by selecting the appropriate choice under the "Start" tab (1820). The user can alter this choice by clicking on the "EDIT" button (1830). After the selected human body representation is presented, the generator invites the user to select a body region (step 520). In the example of FIG. 18, the body region is highlighted as the user moves the cursor over it or clicks on it. The body region selection correlates with the area or zones of the body in which the user is experiencing a medical symptom or complaint. For example, if the user is experiencing sore throat, the user selects the neck or throat region. Similarly, if the user is experiencing nausea, the user selects the stomach or abdomen region. Body regions available for selection are any isolatable surface of the body. Generally, body regions available for selection are those that are associated with particular symptoms. Nonlimiting examples of body regions include: head or scalp, face, neck, throat, chest, breast, abdomen, shoulder, arm, elbow, hand, wrist, fingers, groin, genital region, hip, thigh, knee, leg, ankle, buttocks, back, foot and toes. These body regions may be presented for selection individually or as a group. For example, hand, wrist and fingers may be grouped into one region corresponding to the lower arm, while shoulder, arm and elbow are grouped into one region corresponding to the upper arm. Similarly, leg and ankle can be grouped into one region corresponding to the lower leg, while hip and thigh are grouped into one region corresponding to the upper leg. Likewise, the face region can include eyes, ears, nose and mouth or these regions can be selected separately. While the examples provided above are external body regions, internal body regions, such as organs or muscles, are also within the scope of the invention.

Also, in some implementations, the generator solicits the user to select an orientation for the body representation (e.g., front or back) (1840 in FIG. 18). If the user chooses an orientation, only body regions located in that orientation are available for selection. For example, if the back orientation is chosen, buttocks and back are shown, but chest or breast is not.

Step 530 provides another option for generating input for a health condition query system. In step 530, the generator invites the user to enter search terms by providing a search string input field on the user interface. (1850 in FIG. 18) The user provides the search term by entering it into a designated search field. The search term corresponds to a keyword. Keywords are matched to symptoms in a many to many fashion.

Figure 19:
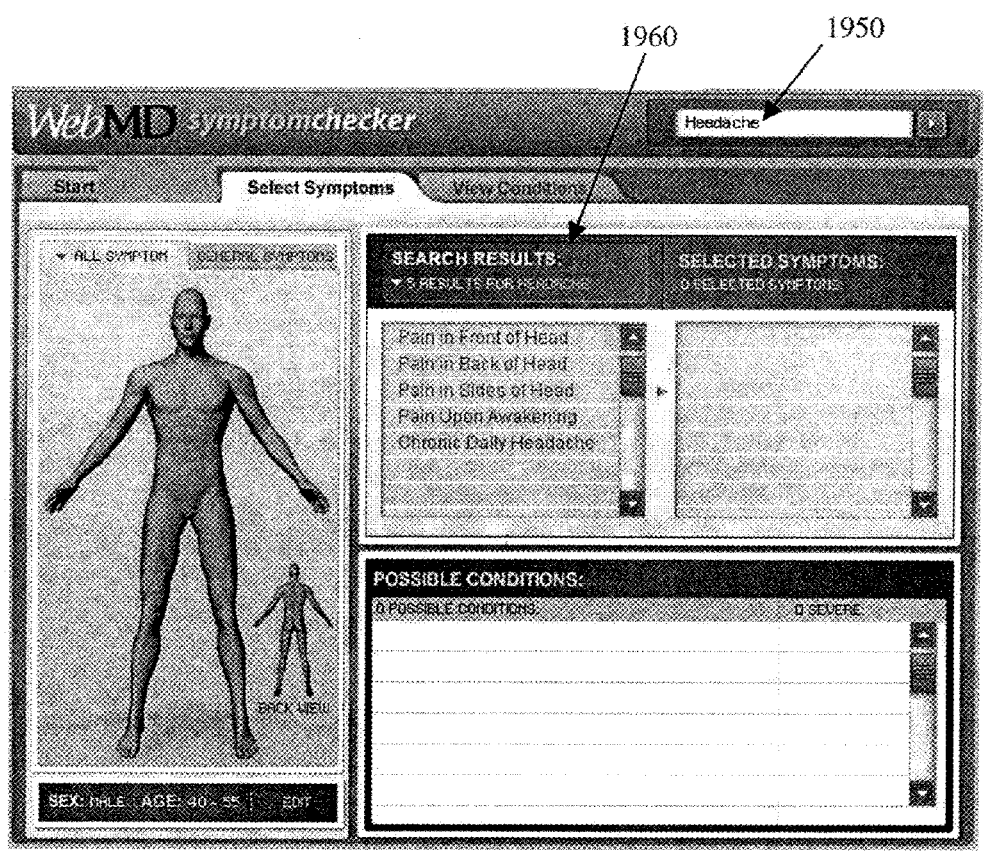
FIG. 19 is an exemplary health condition query system interface showing results for a search string.

Once the user selects a body region (step 520) or a search term (step 530), the generator displays a list of potential symptoms corresponding to the selection or search term (step 540) (1860 in FIG. 18). When input generator 500 is used to generate input for a health condition query system (e.g., 100 or 200), the generator displays symptom information in terms selected from non-professional language. When the user has selected a particular body region (step 520), the generator only presents only symptoms associated with that region. For example, if the user selects the abdomen region, the generator presents symptoms such as nausea, cramps, and gas, but does not present symptoms such as headache, shoulder pain or ankle pain because they are not associated with the abdomen region. As shown in FIG. 18, symptoms relating to the Chest Area are presented (1860). FIG. 19 is another view of the interface of FIG. 18 in which "headache" is entered as a search term (1950) and the generator displays a list of symptoms that match one or more of the keywords entered (1960 in FIG. 19). In some implementations, the generator presents only symptoms that contain all the keywords. For example, if "chronic head pain" is entered, the generator returns only symptoms with that exact name. Alternatively, the generator displays a list of symptoms that contain any of the entered keywords. In step 530, the generator searches all symptoms available, whether or not they are linked to a particular body region.

Figure 20:
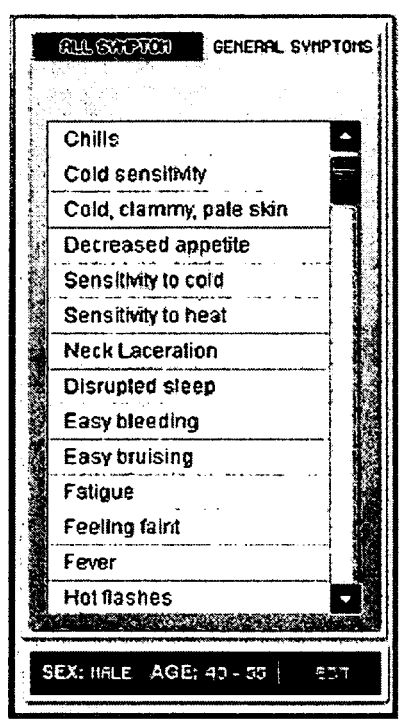
FIG. 20 is an exemplary list of general medical symptoms.

Step 550 provides another option for generating input for a health condition query system. In step 550, the generator presents a list of symptoms that are not specific to a particular body region to the user. In FIG. 18, the generator presents the non-specific symptoms in response to the user selecting the "General Symptoms" tab of the interface (1870). A representative list of general symptoms that would appear under the "General Symptoms" tab is provided in FIG. 20. Such symptoms include, without limitation, symptoms that affect the entire body rather than a specific region. Nonlimiting examples of such symptoms are symptoms related to the skin, fever, general body ache, faintness, vertigo, fatigue, and excessive sweating.

Once symptom information is presented through steps 540 or 550, the generator invites the user to select one or more symptoms (step 560). The user selects symptoms corresponding to his or her present state of health from the lists that correspond to one of the input methods (steps 510, 530, or 550). For example, when symptoms that correspond to a selected body region are displayed, the user selects one or more of the symptoms and the symptoms are added to a symptom list (step 570). In the example of FIG. 18, the user selects one or more symptoms from the possible symptom list (1860) by clicking on the symptom. Once the user selects the symptom, it is entered into the "Selected Symptoms" list (1880). In some implementations, the user selects symptoms from multiple zones. For example, as shown in FIG. 18, the user has selected symptoms from the chest region. If the user is also experiencing headache, the user selects or clicks on the head region and chooses "headache" from the list of possible symptoms. The generator adds "Headache" to the selected symptom list, along with the chest-related symptoms already on the list.

After the user selects one or more symptoms, the health condition query system presents a list of possible medical conditions derived from the selected medical symptoms (570). The health condition query system generates the list of possible medical conditions by analyzing all of the medical symptoms selected by the user. Exemplary methods for deriving possible medical conditions include one or more embodiments described herein. In some embodiments, generation of the health condition query system is dynamic—as symptoms are selected, possible medical conditions are generated and the list of possible medical conditions is updated as more symptoms are added or as the generator received additional information through clarification questions.

Figure 6:
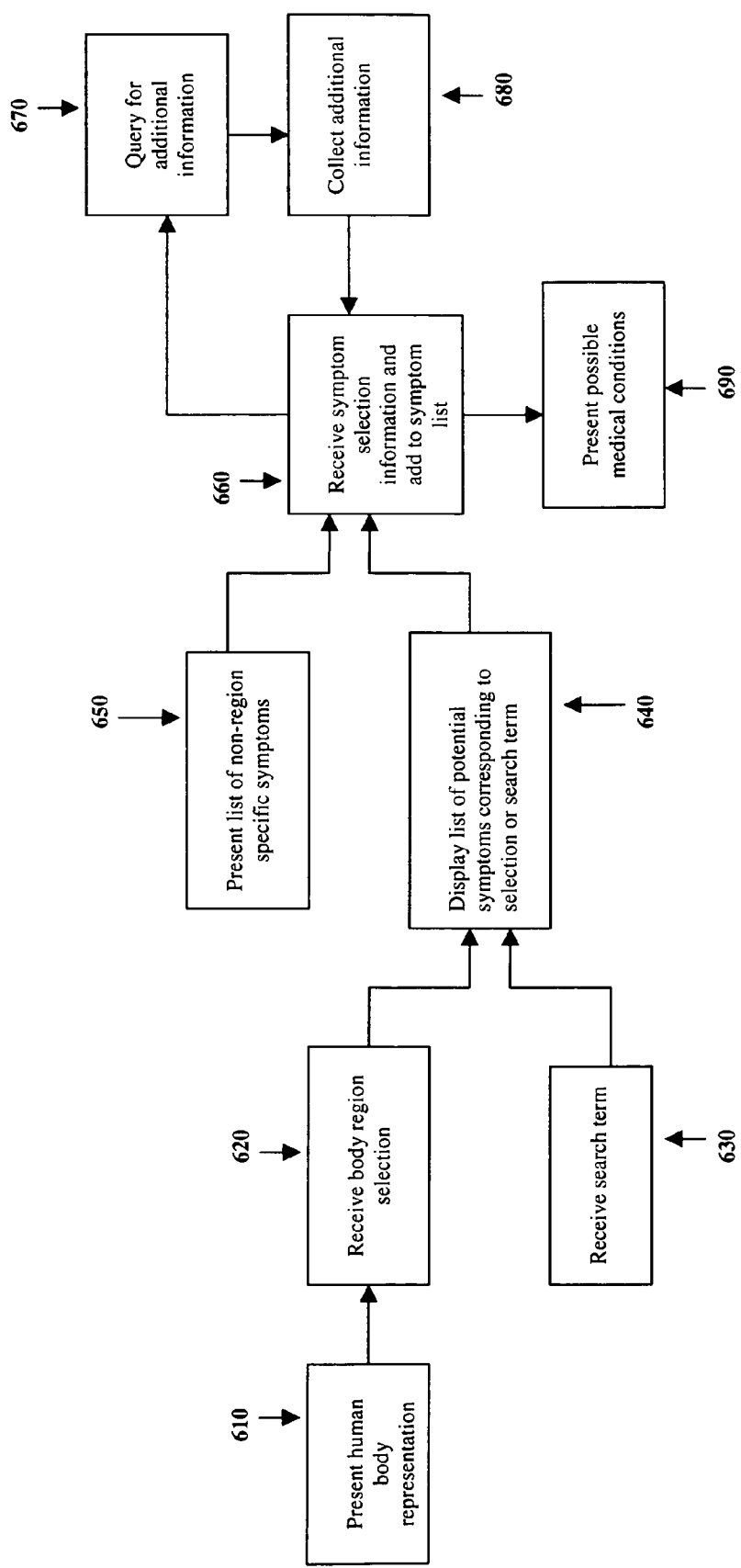
FIG. 6 is a flow diagram of a user interface algorithm in which queries for additional information.
Figure 10:
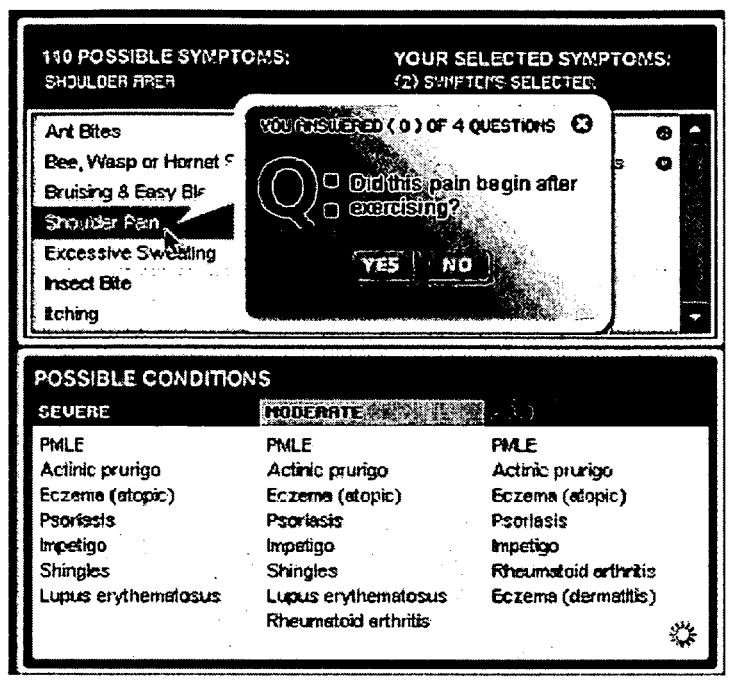
FIG. 10 is an exemplary clarification question interface.
Figure 21:
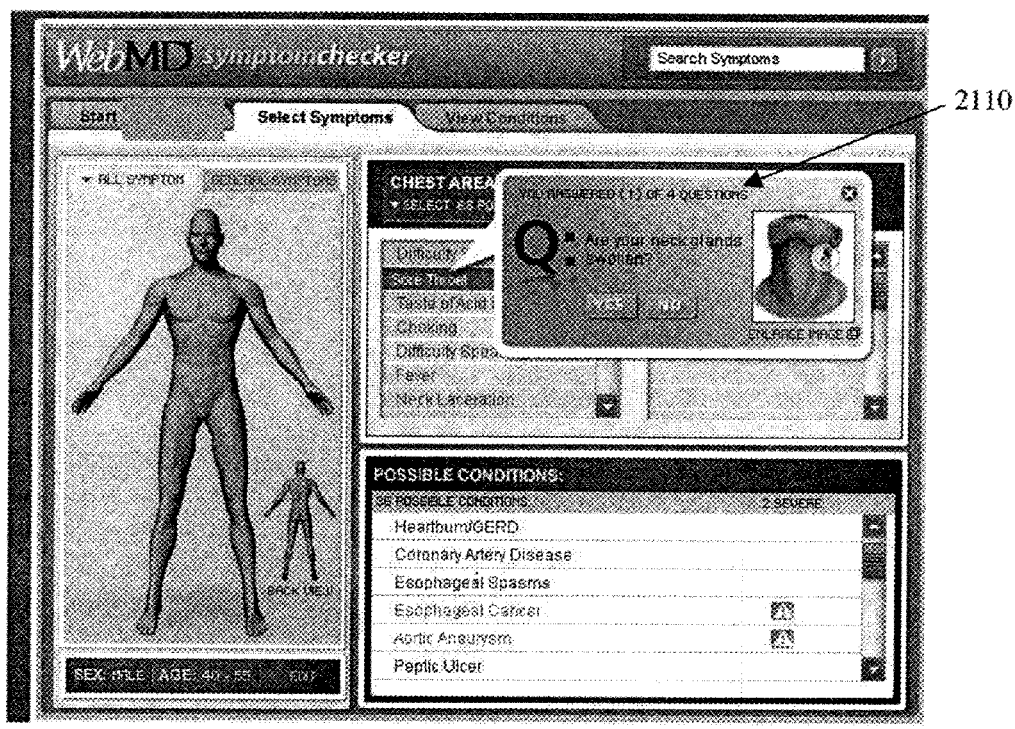
FIG. 21 is an exemplary health condition query system interface with a clarification question.

FIG. 6 is another input generator for a health condition query system. The generator of FIG. 6 is similar to the generator of FIG. 5, with the addition of a clarification algorithm that refines the symptom list for the user's specific health complaints (steps 670-680). Steps 610-660 proceed as described above for steps 510-560 of FIG. 5. The generator invites the user to select symptoms from a list of potential symptoms corresponding to a selected body region, a search term, or a list of non-region specific symptoms and added to a symptom list. In step 670, the clarification algorithm queries for additional health symptom information. The clarification algorithm is similar to the clarification engine associated with health condition query system 100 (FIG. 1, step 170), except that clarification questions are mapped to symptoms rather than conditions or combinations of conditions. Thus, when the user selects a symptom, the algorithm prompts the user for additional information relating to that symptom. One or more clarification questions are mapped to a particular symptom or combination of symptoms. Generally, there is no restriction on the number of clarification questions. In some implementations, one to five clarification questions are used. For example, the symptom "headache" is linked to one or more clarification questions such as "did the headache start suddenly?" or "have you suffered a head injury lately?" FIG. 21 is an example of a user interface showing one of a series of four clarification questions (2110) in response to the symptom "Sore Throat." FIG. 10 is an example of a query for additional information in response to the symptom "shoulder pain." Similarly, FIG. 14 is an example of a query for additional information in response to the symptom "chest pain." Finally, FIG. 16 shows how clarification questions are linked to particular symptoms and also linked to conditions. For example, the clarification engine links the symptom "swollen glands" to the clarification question "Both sides or just one?", which is in turn mapped to the condition "strep throat". Similar clarification questions relate to cough and headache symptoms.

The algorithm user queries with clarification questions either at the time the symptom is selected or after the symptom list is complete. In some implementations, the algorithm does not add the symptom to the symptom list until the user has answered the clarification questions.

Additional symptom information is collected as the user answers the queries for additional information (step 680). The user answers the questions by selecting the appropriate response for his or her state of health. The algorithm then adds the additional symptom information to the symptom list (step 660). For example, if the user selects "yes" for the clarification question "did the headache start suddenly?", that information is added to the symptom list. Similarly, if the user selects "no", the negative information is also added to the symptom list. If the user does not answer the question, or selects "don't know", however, no information is added to the symptom list, as the answer does not further refine the symptom information. In some implementations, the system requires the user to provide an answer to the clarification question. Thus, clarification questions thus provide additional information upon which the possible medical conditions are generated.

As with the input generator described with regard to FIG. 5, as the user selects one or more symptoms, the health condition query system presents a list of possible medical conditions derived from the selected medical symptoms (690).

As described above, the translation engines employ the concept-specific identifiers and corresponding symptom or condition terms that together may form a health terminology thesaurus. Exemplary concept-specific identifiers and corresponding symptom, condition or health information are shown in FIG. 15. The relationships between each concept-specific identifier and the corresponding symptom, condition or health information are stored in a data structure that is in turn stored in local or remote memory or storage and includes a concept-specific identifier (e.g., alphanumeric) and one or more associated symptom or condition terms (or heath information terms). The relationship information stored in the data structure provides uniform identification of symptom or condition concepts despite a variety of lay medical terms and professional medical terms being in use. The listing of concepts in FIG. 15 is not exhaustive of the symptom or condition terms to which the concept-specific identifiers may be applied. To improve search of and access to medical information relating to symptoms and conditions, in one implementation, the concepts (i.e., symptoms, conditions, and other health information) are organized based on their taxonomic and/or semantic relationships, as described in U.S. patent Publication No. 2006/0004607, which is incorporated in its entirety.

Figure 4:
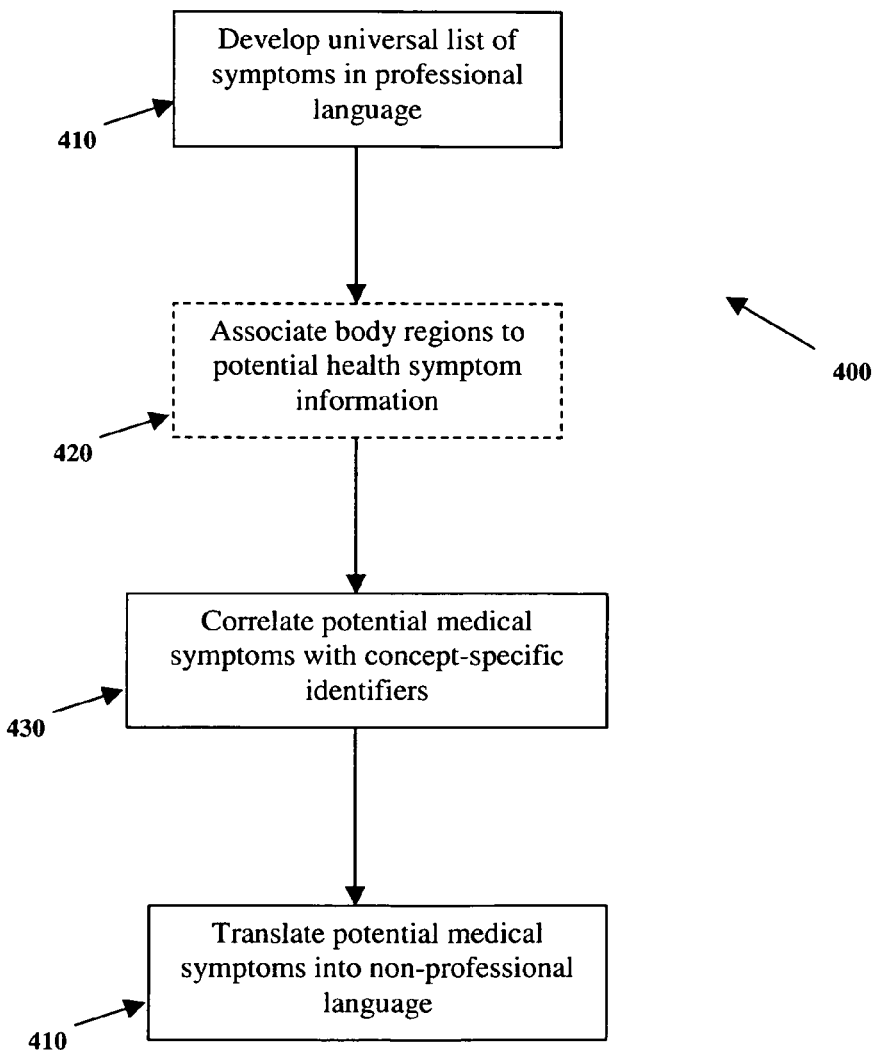
FIG. 4 is a flow diagram of a symptom thesaurus algorithm.

FIG. 4 is a flow diagram of algorithm for creating a symptom thesaurus, 400. The algorithm 400 first develops a universal list of health symptom information (step 410). The algorithm develops the universal list in terminology selected from a professional language. Next, the algorithm optionally correlates body regions to the health symptom information (step 420). For example, nausea and indigestion are correlated with the abdominal region, while itchy eyes and runny nose are correlated with the head or facial region. The algorithm then associates each instance of medical symptom information with a concept-specific identifier (step 430). Finally, the algorithm translates the medical symptoms into terms selected from non-professional language by mapping the concept-specific identifiers to symptoms in non-professional language (step 430). For example, nausea and indigestion are translated to "dyspepsia", while itchy eyes and runny nose are translated to "rhinorrhea".

The concept-specific identifiers also allow the symptom thesaurus to manage synonyms for medical symptoms. Often, many different terms are used by laypeople to describe the same medical symptom. For example, diabetes is sometimes referred to as saccharine diabetes, sugar disease, sugar sickness, or low blood sugar. In some cases, synonyms are regional in nature (e.g., regional colloquialisms), while some synonyms reflect different vernacular or consumer terms. For example, swelling of the feet is referred to as "dropsy" in some areas and back pain is sometimes referred to as lumbago. Associating the same concept-specific identifier to each of these synonymous terms provides for correlation to the proper term for the symptom in professional language. Thus, the algorithm generates a thesaurus, or library, of medical symptoms associated with concept-specific identifiers. The thesaurus may to be used by a health condition query system (e.g., steps 115 or 125 of system 100), either by selecting a symptom in non-professional language or by selecting a symptom in professional language.

Figure 7:
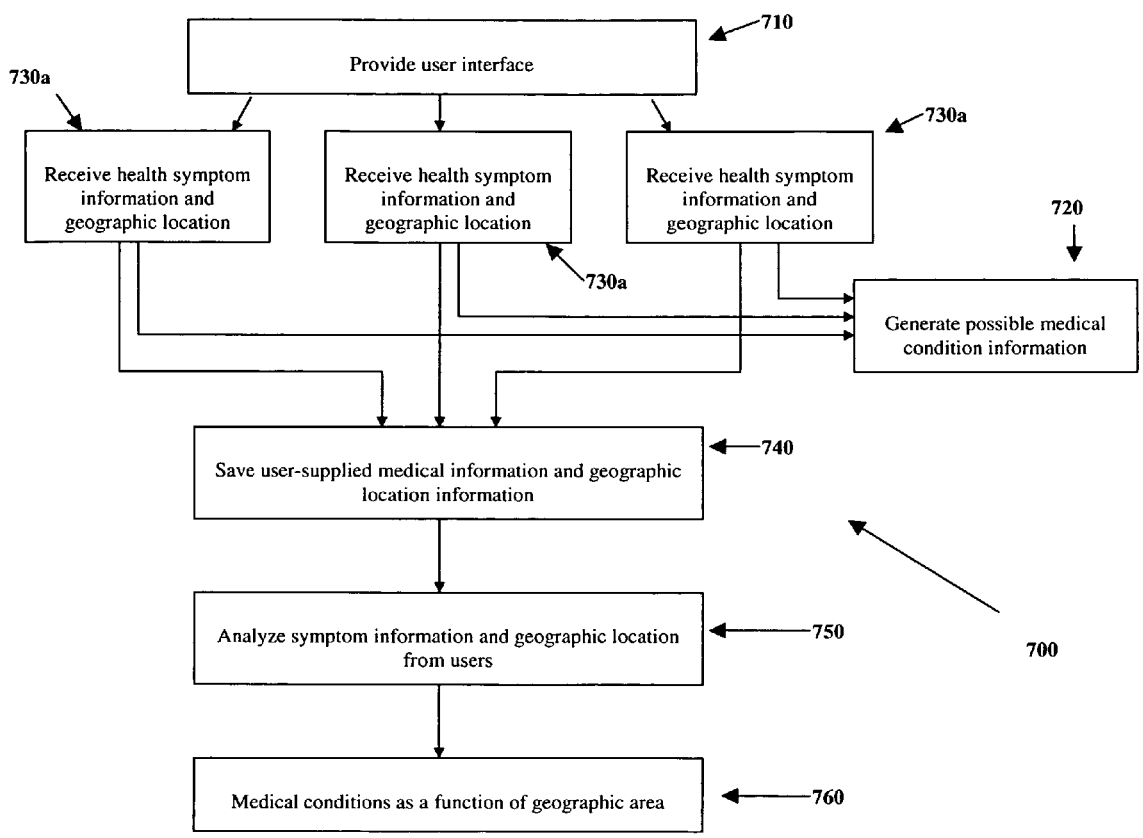
FIG. 7 is a flow diagram for a medical information tracking system.

FIG. 7 is a flow diagram of a condition tracking system (700) that analyzes medical information collected from users of the health condition query systems (e.g., 100 or 200) described above. The system pools the information from users and collectively analyzes it to determine population-wide trends. By linking the user-supplied information to a geographic locator, the system can to provide information about the local prevalence and geographic distribution of user-reported systems and related conditions. Symptom clusters or condition clusters that are tracked using system 700 include contagious diseases (e.g., anthrax, SARS, bird flu, cold, flu, mumps, and measles) as well as conditions that are cyclical or location-specific (e.g., seasonal allergies, Valley fever (coccidiomycosis), and Lyme's disease)

Figure 13:
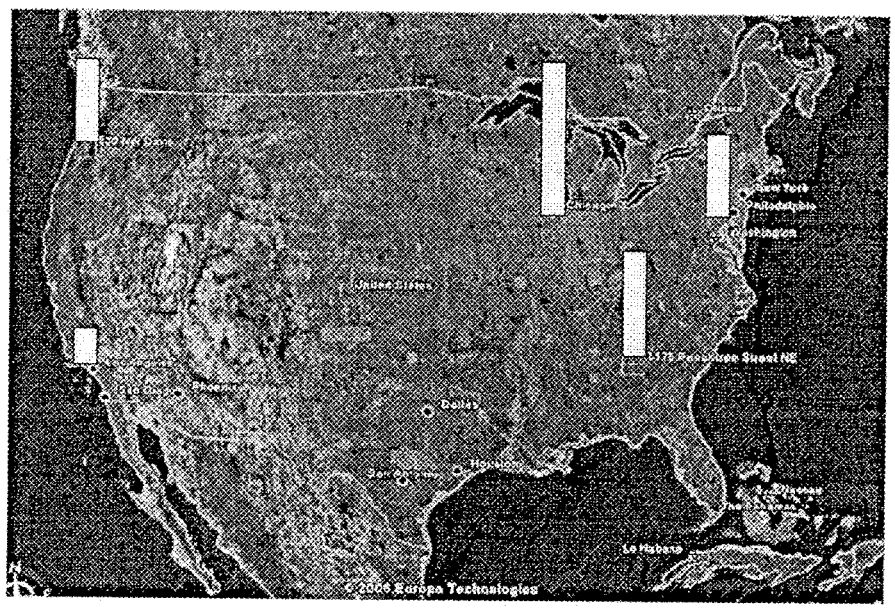
FIG. 13 is exemplary output for a medical information tracking system in pictorial format.

The condition tracking system provides users an interface to a query engine (step 710). Exemplary interfaces used by the system 700 include input generators 500 and 600, described in FIGS. 5 and 6 and also the interface example of FIG. 18. Through the interface, the system receives medical information from multiple users (steps 730a, 730b, 730c). The medical information includes symptom information and other health information, as well as geographic location information (e.g., a zip code, city and/or state, or country). Alternatively, the medical information includes the date and/or time the information was received. In response to receiving symptom information, a health condition query system generates a personalized list of possible medical diagnostic information for each user (step 720). Exemplary health condition query systems include systems 100 and 200 (FIGS. 1 and 2). The system links personal medical information and the geographic location information and saves it for further analysis (step 740). The information is saved locally or remotely. In some implementations, the linked medical geographic location information are saved in user profiles on a server. The system then analyzes the saved symptom information and geographic location information (step 750) on a population-wide basis (i.e., from a plurality of users) and determines medical conditions as a function of geographic area (step 760). The analysis involves identifying clusters of symptoms or conditions in the stored user-supplied information. For example, the system can analyze information to determine the number of users concurrently reporting one or more symptoms that are typical for influenza (e.g., fever, sore throat, muscle ache, headache or fatigue) in specific geographic areas (FIG. 12A)). To assess the emergence, location and/or prevalence of a possible avian influenza outbreak, the system analyzes the stored medical information for the number of users concurrently reporting influenza symptoms as well as one or more atypical symptoms (e.g., conjunctivitis (eye infection), breathing problems (e.g., pneumonia, acute respiratory distress, viral pneumonia), chest pain, diarrhea, or confusion (without breathing problems)) (FIG. 12B). Alternatively, the system analyzes the information to determine geographic areas having the highest incidence of certain symptoms (FIG. 13). The analysis becomes more specific for particular conditions as the information is scrutinized for multiple symptoms associated with a condition.

Figure 8:
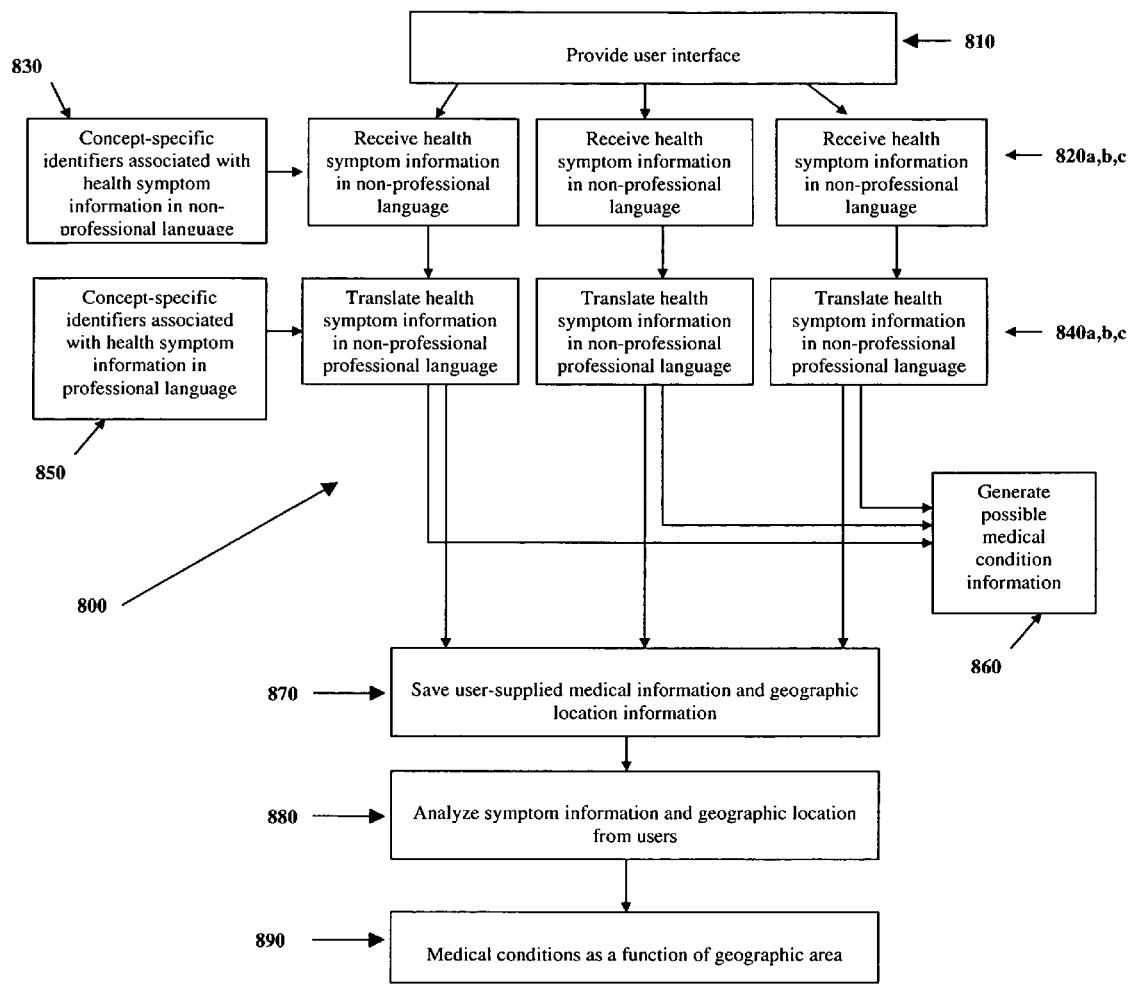
FIG. 8 is a flow diagram for a medical information tracking system in which symptom information is translated from a first language to a second language.

FIG. 8 is flow diagram of another condition tracking system (800) in which the health symptom information is translated from a first langauge to a second language (e.g., non-professional to professional language). The system receives medical information from users and then translates it from non-professional to professional language (steps 840a, 840b, and 840c). The translation engine makes use of concept-specific identifiers associated with medical information in either language type, similar to the translation engines described above (FIGS. 2 and 3).

System 800 presents an interface to a health condition query system (step 810). As with system 700, exemplary interfaces used in system 800 include those described in FIGS. 5 and 6 (systems 500 and 600, respectively). Through the interface, the system receives medical information (from a plurality of users) in non-professional language (steps 820a, 820b, 820c). The information includes a geographic locator. The medical information is associated with concept-specific identifiers (step 830). The system translates the information in non-professional language to professional language by correlating the concept-specific identifiers in non-professional language with concept-specific identifiers associated to medical information in professional language (steps 840a, 840b, 840c and 850). In response to receiving the information, the health condition query system generates a personalized list of possible medical diagnostic information for each user (step 860). Exemplary health condition query systems include systems 100 and 200 (FIGS. 1 and 2). The condition tracking system links the personal medical information and the geographic location information together and saves for further analysis (step 870), as described above. The system then analyzes the saved symptom information and geographic location information are then analyzed (step 880) on a population-wide basis and determines possible medical conditions as a function of geographic area (step 890). As above for system 700, the analysis involves identifying clusters of symptoms or conditions in the stored user-supplied information. System 800 includes analysis of translated information, as well as including the associated concept-specific identifiers in the analysis.

The condition tracking systems generate in tabular format (FIGS. 12A and 12B), graphical format, or a pictorial format suitable for marketing or publication use (e.g., FIG. 13). Public health officials can use output from processes 700 and 800 to determine the incidence of possible medical conditions by geographical area. Besides determining the spread of contagious diseases systems 700 and 800 allow for regional comparisons of various conditions (e.g., prevalence of symptoms or conditions in different cities). For example, the systems can report or display the occurrence of heartburn in New York City versus Chicago. These systems are also useful for providing geographically based medical information directly to consumers, for example through condition reports or condition maps. Such reports and maps can be located on a website accessible to a user or reported through the media.

Figure 17:
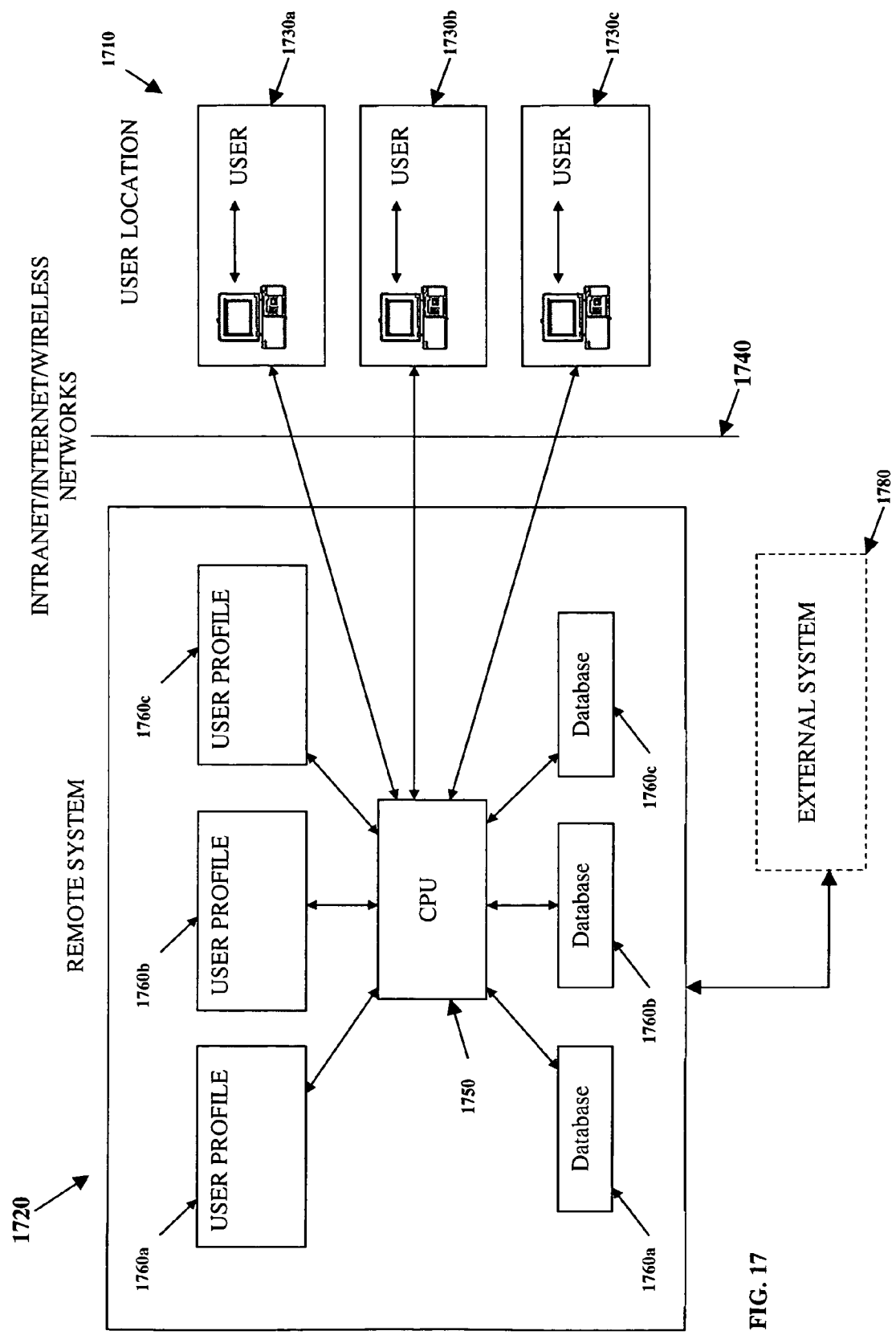
FIG. 17 is a block diagram of an implementation of a computer system that can be used on some of the embodiments of the invention.

The above described systems and algorithms generate personalized health information via a computer network. FIG. 17 is a conceptual diagram of one implementation of the systems and algorithms used in conjunction with the various embodiments described herein. In some implementations, one more users provide input (1730a-c), which a remote system (1720) then processes. In some implementations, the system is a web-based application and the user provides input through a web browser. The user is commonly a lay individual without specific medical training. The computer network (1740) may be private or public and may be a direct connection, a local area network or wide area network, a wireless network or an intranet. In one implementation, possible medical conditions are provided to the user over the Internet. The remote system (1720) is a server or a remote computer, which includes a processing unit (1750), and, optionally one or more databases (1770a-c) and one or more user profiles (1760a-c). As described herein, the user inputs health symptom information through an input device (1730a-c), such as a personal computer, a workstation, or a server terminal. The system transmits the information through the computer network (i.e., over the Internet) to the remote system (1702), which then translates the symptom information to professional language and generates possible medical conditions using databases installed directly on the remote system (1770a-c) or an external system (1780). In some implementations, the system collects additional medical information located in the user's profile (1760a-c), which is stored on the remote system. In some implementations, the user profiles are stored remotely, for example on a separate server or computer, in which case the system imports the information from the separate system. As described above, the systems provide output to the user by conventional means such as through a screen or by hard copy.

The input and output information can be save locally or remotely, including in a user profile.

OTHER EMBODIMENTS

Other embodiments are also within the scope of the invention. While the embodiments presented above illustrate how the invention can be used to generate customized medical information it is understood that the systems and methods of the invention are not limited to the specific embodiments described above. Moreover, while the methods and systems are described in terms of medical information, they are not limited to this application, but rather can be applied to any situation where a first set of concepts are used to generate a second set of concepts.

Although translation is described above in terms of translating medical information in professional terms to non-professional terms, the systems can be used to translate concepts between any two languages (i.e., from a first language to a second language). Similarly, symptom and condition thesauruses are not limited to the terminologies and vocabulary sources described above.

As indicated above, the health condition query systems are not limited to systems incorporating a clarification engine. Similarly, in some implementations the symptom check system does not collect and add personal health information to a symptom list. Moreover, systems within the scope of this invention may not generate an ordered list of possible conditions based on weight coefficients. While the query interface described above is described in terms of a human body representation, it is understood that this method is applicable to any type of animal physiology.

While the systems and algorithms presented here are described as systems in which a user provides input, the systems and algorithms are not limited solely to applications in which a user supplies input. For example, health symptom information or additional health information can be provided through networks or data downloads from other systems containing information useful for generating possible medical conditions. Moreover, the systems and algorithms can be used in other applications and environments, such as in a system for questioning patients for medical information, or in a system for collecting triage information about a patient. In these systems, a user or someone in the position of evaluating a patient may supply the information.

It is to be understood that while the invention has been described in conjunction with the detailed description thereof, the foregoing description is intended to illustrate and not limit the scope of the invention. Other aspects, advantages, and modifications are within the scope of the following claims. Furthermore, it will be recognized embodiments can be modified in arrangement and detail without departing from the principles of the invention. It should be understood that the programs, processes, or methods described herein are not related or limited to any particular type of computer apparatus, unless indicated otherwise.

We claim:

1. A computer-implemented method for generating a diagnosis based on identified symptoms associated with a patient, said method comprising:

in a computer system, receiving a list of symptoms associated with the patient specified in terms selected from a first language set;

in the computer system, translating the list of symptoms that are specified in terms selected from the first language set into a translated list of symptoms specified in terms selected from a second language set;

based on the translated list of symptoms, in the computer system, generating possible medical conditions, said possible medical conditions described in terms of the second language set;

in the computer system, translating the possible medical conditions into descriptions that are specified in terms selected from the first language set, wherein the first and second language sets are both natural language sets, and wherein natural language sets are sets of words used for human communication;

assigning a probability weight coefficient to each of the possible medical conditions based on a presence of one or more symptoms that exclude a possible condition and at least one of (i) clustering or pattern recognition of symptoms to possible conditions, and (ii) whether the patient is associated with a geographical location that is also associated with at least one of the possible medical conditions; and generating an ordered list of possible medical conditions associated with the patient based on the assigned weight coefficients.

2. The method of claim 1, wherein the first language set is non-professional medical language.

3. The method of claim 1, wherein the second language set is professional medical language.

4. The method of claim 1, further comprising receiving additional personal health information and wherein generating the possible medical conditions is also based on the personal health information.

5. The method of claim 4, wherein the additional personal health information is at least one of age, gender, or medication information.

6. The method of claim 1, wherein the received list of symptoms is received from one or more of user input or an external data source.

7. The method of claim 6, wherein the external data source is at least one of a health profile associated with the patient, public health information, or a health tracking system.

8. The method of claim 1, wherein the translating the list of symptoms comprises correlating concept-specific identifiers associated with the symptoms specified in terms selected from the first language set with concept-specific identifiers associated with the symptoms specified in terms selected from the second language set.

9. The method of claim 1, further comprising exporting the translated list of symptoms to an external system.

10. The method of claim 1, further comprising:

via the computer system, querying for additional symptom information based on one or more of the following: one or more symptoms and one or more possible medical conditions;

receiving additional symptom information; and in the computer system, adding the additional symptom information to the list of symptoms.

11. The method of claim 1, wherein the translated list of symptoms is added to a profile associated with the patient.

12. The method of claim 1, wherein one or more of the possible medical conditions are added to a profile associated with the patient.

13. The method of claim 1, further comprising providing possible medical treatment information in non-professional language, wherein the possible medical treatment information corresponds to one of the possible medical conditions.

14. The method of claim 1, wherein the list of symptoms is generated by a method comprising:

via the computer system presenting a representation of a human body to a user through a visual display;

defining a plurality of regions within the representation of the human body;

via the computer system receiving input from the user selecting a particular one of the plurality of regions;

in response to the received input, displaying to the user a list of medical symptoms associated with the selected region; and enabling the user to select symptoms from the displayed list of symptoms.

15. The method of claim 14, further comprising:

querying the user for additional symptom information based on one or more symptoms selected by the user; and adding the additional symptom information to the list of symptoms.

16. The method of claim 1, further comprising assigning a severity weight coefficient to each of the possible medical conditions; and alerting a user if a severe condition is present.

17. The method of claim 1, further comprising assigning an urgency weight coefficient to each of the possible medical conditions; and alerting a user if an urgent condition is present.

18. The method of claim 1, further comprising receiving medical information associated with at least one other patient, wherein the medical information includes geographical location information; and analyzing the medical information to determine population-wide trends, including geographical distributions of user-reported conditions.

19. The method of claim 18 wherein the medical information associated with the at least one other patient comprises at least one of a second list of symptoms associated with the at least one other patient, and a second ordered list of possible medical conditions associated with the at least one other patient.

20. A computer system for generating a diagnosis based on identified symptoms associated with a patient, the system having a computer configured to execute instructions stored on a memory, said system comprising:

an interface configured to receive a list of symptoms associated with the patient specified in terms selected from a first language set;

a translation engine configured to translate the list of symptoms that are specified in terms selected from the first language set into a translated list of symptoms specified in terms selected from a second language set;

an analysis module configured to generate possible medical conditions using the translated list of symptoms, said possible medical conditions described in terms of the second language set;

wherein the translation engine is also configured to translate the possible medical conditions generated by the analysis module into descriptions that are specified in terms selected from the first language set, wherein the first and second language sets are both natural language sets, and wherein natural language sets are sets of words used for human communication;

an assignor configured to assign a probability weight coefficient to each of the possible medical conditions based on a presence of one or more symptoms that exclude a possible condition and at least one of (i) clustering or pattern recognition of symptoms to possible conditions, and (ii) whether the patient is associated with a geographical location that is also associated with at least one of the possible medical conditions; and wherein the analysis module is also configured to generate an ordered list of possible medical conditions associated with the patient based on the assigned weight coefficients.

21. The system of claim 20, further comprising:

a query engine configured to query for additional symptom information based on one or more of the following: one or more symptoms and one or more possible medical conditions, receive additional symptom information, and add the additional symptom information to the list of symptoms.

22. The system of claim 20, wherein the interface comprises a representation of a human body presented to a user through a visual display, wherein a plurality of regions are defined within the representation of the human body;

the interface is configured to receive input from the user selecting a particular one of the plurality of regions; and the interface is configured to display to the user a list of medical symptoms associated with the selected region and is configured to enable the user to select a plurality of symptoms from the displayed list of symptoms.

23. The system of claim 20, wherein the interface is configured to receive a list of symptoms specified in terms of a non-professional medical language set and wherein the first language set is the non-professional medical language set.

24. The system of claim 23, wherein the translation engine is configured to translate the list of symptoms into the translated list of symptoms specified in terms selected from a professional medical language set and wherein the second language set is the professional medical language set.

25. The system of claim 20, wherein the translation engine is configured to correlate concept-specific identifiers associated with the symptoms specified in terms selected from the first language set with concept-specific identifiers associated with the symptoms specified in terms selected from the second language set.

26. The system of claim 20, wherein the assignor is further configured to assign a severity weight coefficient to each of the possible medical conditions; and wherein the analysis module is configured to alert a user if a severe condition is present.

27. The system of claim 20, wherein the assignor is further configured to assign an urgency weight coefficient to each of the possible medical conditions; and wherein the analysis module is configured to alert a user if an urgent condition is present.

28. The system of claim 20, wherein the interface is further configured to receive medical information associated with at least one other patient, wherein the medical information includes geographical location information; and wherein the analysis module is configured to analyze the medical information to determine population-wide trends, including geographical distributions of user-reported conditions.

29. The system of claim 28, wherein the medical information associated with at least one other patient comprises at least one of a second list of symptoms associated with the at least one other patient, and a second ordered list of possible medical conditions associated with the at least one other patient.

* * * * *